(12) United States Patent
Wu et al.

US008541543B2

(10) Patent No.: US 8,541,543 B2
(45) Date of Patent: Sep. 24, 2013

(54) PEPTIDES SPECIFIC FOR HEPATOCELLULAR CARCINOMA CELLS AND APPLICATIONS THEREOF

(75) Inventors: Han-Chung Wu, Taipei (TW);
Chin-Tarng Lin, Taipei (TW); Albert Lo, Minsyong Township, Chiayi County (TW)

(73) Assignee: Academia Sinica, Taipei (TW)

(*) Notice: Subject to any disclaimer, the term of this patent is extended or adjusted under 35 U.S.C. 154(b) by 502 days.

(21) Appl. No.: 12/292,401

(22) Filed: Nov. 18, 2008

(65) Prior Publication Data
US 2009/0136418 A1  May 28, 2009

Related U.S. Application Data

(60) Provisional application No. 60/996,488, filed on Nov. 20, 2007.

(51) Int. Cl.
*C07K 5/00* (2006.01)
(52) U.S. Cl.
USPC .................. 530/300; 530/391.7; 424/450
(58) Field of Classification Search
None
See application file for complete search history.

(56) References Cited

U.S. PATENT DOCUMENTS

| | | | |
|---|---|---|---|
| 4,179,337 | A | 12/1979 | Davis et al. |
| 4,301,144 | A | 11/1981 | Iwashita et al. |
| 4,496,689 | A | 1/1985 | Mitra |
| 4,640,835 | A | 2/1987 | Shimizu et al. |
| 4,670,417 | A | 6/1987 | Iwasaki et al. |
| 4,791,192 | A | 12/1988 | Nakagawa et al. |
| 4,816,567 | A | 3/1989 | Cabilly et al. |
| 5,283,317 | A | 2/1994 | Saifer et al. |
| 6,051,251 | A | 4/2000 | Zalipsky et al. |
| 6,355,267 | B1 | 3/2002 | Collins |
| 6,663,885 | B1 | 12/2003 | Hager et al. |
| 6,974,884 | B2 | 12/2005 | Raines et al. |
| 2005/0010036 | A1* | 1/2005 | Wu et al. .............. 530/388.8 |
| 2006/0160743 | A1* | 7/2006 | Zhang et al. .............. 514/15 |

FOREIGN PATENT DOCUMENTS
WO   WO 95/34326   12/1995

OTHER PUBLICATIONS

Burgess et al, Journal of Cell biology, vol. 111, p. 2129-2138, 1990.*
Lin et al Biochemistry USA, vol. 14, p. 1559-1563, 1975.*
Lo Albert, "Identification of a Novel Peptide Ligand for Targeted Drug Delivery against Hepatocellular Carcinoma," Graduate Thesis No. R94444001, indexed and shelved at the National Taiwanese University Library on Sep. 4, 2007.
Partial International Search Report, mailed Apr. 1, 2009, in related International application No. PCT/US2008/084043.
Han et al: "Pathogenomic sequence analysis of *Bacillus cereus* and *Bacillus thuringiensis* isolates closely related to *Bacillus anthracis*" Journal of Bacteriology, American Society for Microbiology, US, vol. 188, No. 9, May 1, 2006, pp. 3382-3390.
Du et al: "In vitro panning of a targeting peptide to hepatocarcinoma from a phage display peptide library" Biochemical and Biophysical Research Communications, Academic Press Inc. Orlando, FL, US, vol. 342, No. 3, Apr. 14, 2006, pp. 956-962.
Allen: "Ligand-targeted therapeutics in anticancer therapy" Nature Reviews. Cancer, Natur Publishing Group, London, GB, vol. 2, No. 10, Oct. 1, 2002, pp. 750-763.
Krumpe et al: "The Use of Phase-Displayed Peptide Libraries to Develop Tumor-Targeting Drugs" International Journal of Peptide Research and Therapeutics; Formerly Known As Ketters in Peptide Science, Kluwer Academic Publishers, DO, vol. 12, No. 1, Mar. 1, 2006, pp. 79-91.
Halm U et al: "A phase II study of pegylated liposomal doxorubicin for treatment of advanced hepatocellular carcinoma." Annals of Oncology: Official Journal of the European Society for Medical Oncology / ESMO Jan. 2000, vol. 11, No. 1, Jan. 2000, pp. 113-114.
International Preliminary Report on Patentability, mailed Jun. 3, 2010, in International Patent Application No. PCT/US2008/084043.
Al-Batran, S. E., Bischoff, J., von Minckwitz, G., Atmaca, A., Kleeberg, U., Meuthen, I., Morack, G., Lerbs, W., Hecker, D., Sehouli, J., Knuth, A., and Jager, E. (2006) The clinical benefit of pegylated liposomal doxorubicin in patients with metastatic breast cancer previously treated with conventional anthracyclines: a multicentre phase II trial. Br J Cancer 94, 1615-1620.
Allen, T. M., and Cullis, P. R. (2004) Drug delivery systems: entering the mainstream. Science 303, 1818-1822.
Allen, T. M., Mumbengegwi, D. R., and Charrois, G. J. (2005) Anti-CD19-targeted liposomal doxorubicin improves the therapeutic efficacy in murine B-cell lymphoma and ameliorates the toxicity of liposomes with varying drug release rates. Clin Cancer Res 11, 3567-3573.
Altschul et al. (1990). Basic Local Alignment Search Tool. J. Mol. Biol., 215:403-410.
Arap, W., Pasqualini, R., and Ruoslahti, E. (1998) Cancer treatment by targeted drug delivery to tumor vasculature in a mouse model. Science 279, 377-380.

(Continued)

*Primary Examiner* — Lei Yao
(74) *Attorney, Agent, or Firm* — Finnegan, Henderson, Farabow, Garrett & Dunner, LLP

(57) ABSTRACT

Hepatocellular carcinoma (HCC) is the fourth leading cause of cancer death worldwide. Novel treatment strategies derived from increased knowledge of molecular oncology are constantly being developed to cure this disease. Here, we used phage display to identify novel peptides, including (SP94), which binds specifically to HCC cells. In vitro, the phage clone PC94 binds to HCC cell lines. In vivo, PC94 homed specifically to tumor tissues but not to normal visceral organs in SCID mice bearing human HCC xenografts. The homing ability could be competitively inhibited by synthetic peptide, SP94. PC94 localized to tumor tissues but could not be detected in SP94-competed tumor tissues or in normal organs. In addition, PC94 recognized the tumor tissue but not non-tumor tissue in surgical specimens from HCC patients, with a positive rate of 61.3% (19/31). With the conjugation of SP94 and liposomal doxorubicin, a targeted drug delivery system enhanced the therapeutic efficacy against HCC xenografts through enhanced tumor apoptosis and decreased tumor angiogenesis. Our results indicate that SP94 can improve the systemic treatment of patients with advanced HCC.

Figure 1:
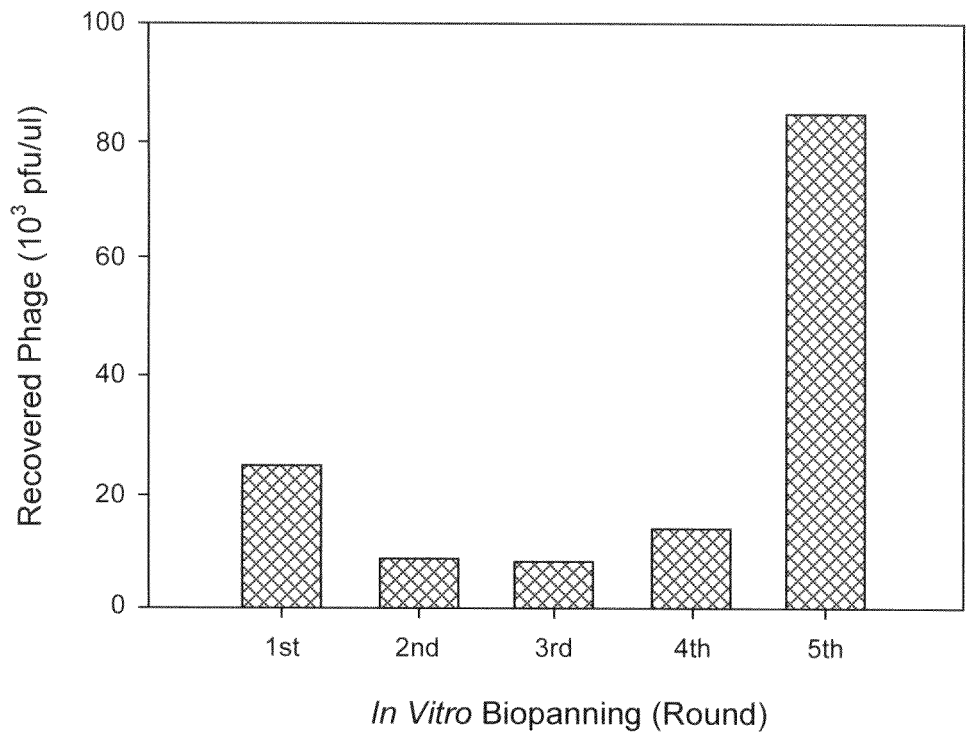

9 Claims, 12 Drawing Sheets
(6 of 12 Drawing Sheet(s) Filed in Color)

(56) References Cited

OTHER PUBLICATIONS

Bartel P, Chien CT, Sternglanz R, Fields S. (1993). Elimination of false positives that arise in using the two-hybrid system. Biotechniques 14:920-924.

Bird et al. (1988) Single-Chain Antigen-Binding Proteins. Science 242:423-426.

Bosslet, K., Straub, R., Blumrich, M., Czech, J., Gerken, M., Sperker, B., Kroemer, H. K., Gesson, J. P., Koch, M., and Monneret, C. (1998) Elucidation of the mechanism enabling tumor selective prodrug monotherapy. Cancer Res 58, 1195-1201.

Burroughs, A., Hochhauser, D., and Meyer, T. (2004) Systemic treatment and liver transplantation for hepatocellular carcinoma: two ends of the therapeutic spectrum. Lancet Oncol 5, 409-418.

Lasic DD, Ceh B, Stuart MC, Guo L, Frederik PM, Barenholz Y. (1995) Transmembrane gradient driven phase transitions within vesicles: lessons for drug delivery. Biochim Biophys Acta. Nov. 1, 1995;1239(2):145-56.

Ceh B, Lasic DD. (1997) A Rigorous Theory of Remote Loading of Drugs into Liposomes: Transmembrane Potential and Induced pH-Gradient Loading and Leakage of Liposomes. J Colloid Interface Sci. Jan. 1, 1997;185(1):9-18.

Chen, Y. C., Huang, H. N., Lin, C. T., Chen, Y. F., King, C. C., and Wu, H. C. (2007) Generation and characterization of monoclonal antibodies against dengue virus type 1 for epitope mapping and serological detection by epitope-based peptide antigens. Clin Vaccine Immunol 14, 404-411.

Chu, Y. W., Yang, P. C., Yang, S. C., Shyu, Y. C., Hendrix, M. J., Wu, R., and Wu, C. W. (1997). Selection of invasive and metastatic subpopulations from a human lung adenocarcinoma cell line. American journal of respiratory cell and molecular biology 17, 353-360.

Clackson et al. (1991) Making antibody fragments using phage display libraries. Nature 352: 624-628.

De Vita F, Orditura M, Infusino S, Martinelli E, Merola MC, Morgillo F, Cosenza A, Di Martino N, Del Genio A, Catalano G. (2001). Preoperative chemo-radiotherapy for carcinoma of the esophagus. Tumori. 87, S24-7.

Duncan, R. (2003) The dawning era of polymer therapeutics. Nat Rev Drug Discov 2, 347-360.

Farazi, P. A., and DePinho, R. A. (2006) Hepatocellular carcinoma pathogenesis: from genes to environment. Nat Rev Cancer 6, 674-687.

Giordano, R. J., Cardo-Vila, M., Lahdenranta, J., Pasqualini, R., and Arap, W. (2001) Biopanning and rapid analysis of selective interactive ligands. Nat Med 7, 1249-1253.

Grant, G. (1992) Synthetic Peptides, A Users Guide, W.H. Freeman and Co. Chapter 3.

Harrington, K. J., Mohammadtaghi, S., Uster, P. S., Glass, D., Peters, A. M., Vile, R. G., and Stewart, J. S. (2001) Effective targeting of solid tumors in patients with locally advanced cancers by radiolabeled pegylated liposomes. Clin Cancer Res 7, 243-254.

Hashizume, H., Baluk, P., Morikawa, S., McLean, J. W., Thurston, G., Roberge, S., Jain, R. K., and McDonald, D. M. (2000) Openings between defective endothelial cells explain tumor vessel leakiness. Am J Pathol 156, 1363-1380.

Hermanson, G.T. (1996) Bioconjugate Techniques; Academic Press. Chapters 3 and 9.

Hoffman, J. A., Giraudo, E., Singh, M., Zhang, L., Inoue, M., Porkka, K., Hanahan, D., and Ruoslahti, E. (2003) Progressive vascular changes in a transgenic mouse model of squamous cell carcinoma. Cancer Cell 4, 383-391.

Hong, R. L., and Tseng, Y. L. (2001) Phase I and pharmacokinetic study of a stable, polyethylene-glycolated liposomal doxorubicin in patients with solid tumors: the relation between pharmacokinetic property and toxicity. Cancer 91, 1826-1833.

Hong, R. L., and Tseng, Y. L. (2003) A phase II and pharmacokinetic study of pegylated liposomal doxorubicin in patients with advanced hepatocellular carcinoma. Cancer Chemother Pharmacol 51, 433-438.

Hong, R. L., Huang, C. J., Tseng, Y. L., Pang, V. F., Chen, S. T., Liu, J. J., and Chang, F. H. (1999) Direct comparison of liposomal doxorubicin with or without polyethylene glycol coating in C-26 tumor-bearing mice: is surface coating with polyethylene glycol beneficial? Clin Cancer Res 5, 3645-3652.

Hug, P., and Sleight R.G. (1991). Liposomes for the transformation of eukaryotic cells. Biochim Biophys Acta. 1097, 1-17.

Hunkapiller et al. (1984) A microchemical facility for the analysis and synthesis of genes and proteins. Nature 310:105-111.

Huston et al. (1988) Protein engineering of antibody binding sites: recovery of specific activity in an anti-digoxin single-chain Fv analogue produced in *Escherichia coli*. Proc. Natl. Acad. Sci. USA 85:5879-5883.

Iwabuchi K, Li B, Bartel P, and Fields S. (1993). Use of the two-hybrid system to identify the domain of p53 involved in oligomerization. Oncogene 8:1693-1696.

Jain, R. K. (1987) Transport of molecules in the tumor interstitium: a review. Cancer Res 47, 3039-3051.

Jemal, A., Murray, T., Ward, E., Samuels, A., Tiwari, R. C., Ghafoor, A., Feuer, E. J., and Thun, M. J. (2005) Cancer statistics. CA Cancer J Clin 55, 10-30.

Joyce, J. A., Laakkonen, P., Bernasconi, M., Bergers, G., Ruoslahti, E., and Hanahan, D. (2003) Stage-specific vascular markers revealed by phage display in a mouse model of pancreatic islet tumorigenesis. Cancer Cell 4, 393-403.

Kohler and Milstein (1975) Continuous cultures of fused cells secreting antibody of predefined specificity. Nature 256:495-499.

Kreitman and Pastan, Immunotoxins in the treatment of hematologic malignancies. Curr Drug Targets. 7:1301-11 (2006).

Lee, T. Y., Lin, C. T., Kuo, S. Y., K., C. D., and Wu, H. C. (2007) Tumor-homing peptides with targeting to tumor blood vessels of lung cancer for drug delivery. Cancer Research 67, 10958-10965.

Lee, T. Y., Wu, H. C., Tseng, Y. L., and Lin, C. T. (2004) A novel peptide specifically binding to nasopharyngeal carcinoma for targeted drug delivery. Cancer Res 64, 8002-8008.

Lichtenberg and Barenholz (1988) Liposomes: preparation, characterization, and preservation. Methods of Biochemical Analysis, vol. 33, 337-462.

Lin, C. T., Wong, C. I., Chan, W. Y., Tzung, K. W., Ho, J. K., Hsu, M. M., and Chuang, S. M. (1990). Establishment and characterization of two nasopharyngeal carcinoma cell lines. Laboratory investigation; a journal of technical methods and pathology 62, 713-724.

Liu, I. J., Hsueh, P. R., Lin, C. T., Chiu, C. Y., Kao, C. L., Liao, M. Y., and Wu, H. C. (2004) Disease-specific B Cell epitopes for serum antibodies from patients with severe acute respiratory syndrome (SARS) and serologic detection of SARS antibodies by epitope-based peptide antigens. The Journal of infectious diseases 190, 797-809.

MacDiarmid, J. A., Mugridge, N. B., Weiss, J. C., Phillips, L., Burn, A. L., Paulin, R. P., Haasdyk, J. E., Dickson, K. A., Brahmbhatt, V. N., Pattison, S. T., James, A. C., Al Bakri, G., Straw, R. C., Stillman, B., Graham, R. M., and Brahmbhatt, H. (2007) Bacterially derived 400 nm particles for encapsulation and cancer cell targeting of chemotherapeutics. Cancer Cell 11, 431-445.

Madura, K., Dohmen, R.J., and Varshaysky, A. (1993) N-recognin/Ubc2 interactions in the N-end rule pathway. J. Biol. Chem. 268:12046-12054.

Marks et al. (1991) By-passing Immunization Human Antibodies from V-gene Libraries Displayed on Phage. J. Mol. Biol. 222:581-597.

Matsumura, Y., and Maeda, H. (1986) A new concept for macromolecular therapeutics in cancer chemotherapy: mechanism of tumoritropic accumulation of proteins and the antitumor agent smancs. Cancer Res 46, 6387-6392.

Monfardini, C., et al. (1995) A branched monomethoxypoly(ethylene glycol) for protein modification. Bioconjugate Chem. 6:62-69.

Mori, T. (2004) Cancer-specific ligands identified from screening of peptide-display libraries. Curr Pharm Des 10, 2335-2343.

Muggia, F. M., Hainsworth, J. D., Jeffers, S., Miller, P., Groshen, S., Tan, M., Roman, L., Uziely, B., Muderspach, L., Garcia, A., Burnett, A., Greco, F. A., Morrow, C. P., Paradiso, L. J., and Liang, L. J. (1997) Phase II study of liposomal doxorubicin in refractory ovarian cancer: antitumor activity and toxicity modification by liposomal encapsulation. J Clin Oncol 15, 987-993.

Myers et al. (1988) Optimal alignments in linear space. Comput. Appl. Biosci., 4:11-17.

Needleman et al. (1970) A General Method Applicable to the Search for Similarities in the Amino Acid Sequence of Two Proteins. J. Mol. Biol., 48:443-453.

Ng EW, Shima DT, Calias P, Cunningham ET Jr, Guyer DR, Adamis AP (2006) Pegaptanib, a targeted anti-VEGF aptamer for ocular vascular disease. Nat Rev Drug Discov. 5, 123-32.

Northfelt, D. W., Dezube, B. J., Thommes, J. A., Miller, B. J., Fischl, M. A., Friedman-Kien, A., Kaplan, L. D., Du Mond, C., Mamelok, R. D., and Henry, D. H. (1998) Pegylated-liposomal doxorubicin versus doxorubicin, bleomycin, and vincristine in the treatment of AIDS-related Kaposi's sarcoma: results of a randomized phase III clinical trial. J Clin Oncol 16, 2445-2451.

Northfelt, D. W., Martin, F. J., Working, P., Volberding, P. A., Russell, J., Newman, M., Amantea, M. A., and Kaplan, L. D. (1996) Doxorubicin encapsulated in liposomes containing surface-bound polyethylene glycol: pharmacokinetics, tumor localization, and safety in patients with AIDS-related Kaposi's sarcoma. J Clin Pharmacol 36, 55-63.

Papahadjopoulos, D., Allen, T. M., Gabizon, A., Mayhew, E., Matthay, K., Huang, S. K., Lee, K. D., Woodle, M. C., Lasic, D. D., Redemann, C., and et al. (1991) Sterically stabilized liposomes: improvements in pharmacokinetics and antitumor therapeutic efficacy. Proc Natl Acad Sci U S A 88, 11460-11464.

Pastorino, F., Brignole, C., Di Paolo, D., Nico, B., Pezzolo, A., Marimpietri, D., Pagnan, G., Piccardi, F., Cilli, M., Longhi, R., Ribatti, D., Corti, A., Allen, T. M., and Ponzoni, M. (2006) Targeting liposomal chemotherapy via both tumor cell-specific and tumor vasculature-specific ligands potentiates therapeutic efficacy. Cancer Res 66, 10073-10082.

Ranson, M. R., Carmichael, J., O'Byrne, K., Stewart, S., Smith, D., and Howell, A. (1997) Treatment of advanced breast cancer with sterically stabilized liposomal doxorubicin: results of a multicenter phase II trial. J Clin Oncol 15, 3185-3191.

Satchi-Fainaro, R., Mamluk, R., Wang, L., Short, S. M., Nagy, J. A., Feng, D., Dvorak, A. M., Dvorak, H. F., Puder, M., Mukhopadhyay, D., and Folkman, J. (2005) Inhibition of vessel permeability by TNP-470 and its polymer conjugate, caplostatin. Cancer Cell 7, 251-261.

Schmidinger, M., Wenzel, C., Locker, G. J., Muehlbacher, F., Steininger, R., Gnant, M., Crevenna, R., and Budinsky, A. C. (2001) Pilot study with pegylated liposomal doxorubicin for advanced or unresectable hepatocellular carcinoma. Br J Cancer 85, 1850-1852.

Shadidi, M., and Sioud, M. (2003) Identification of novel carrier peptides for the specific delivery of therapeutics into cancer cells. Faseb J 17, 256-258.

Stefano et al. (2006) A conjugate of doxorubicin with lactosaminated albumin enhances the drug concentrations in all the forms of rat hepatocellular carcinomas independently of their differentiation grade. Liver Int. 26, 726-33.

Stewart, S., Jablonowski, H., Goebel, F. D., Arasteh, K., Spittle, M., Rios, A., Aboulafia, D., Galleshaw, J., and Dezube, B. J. (1998) Randomized comparative trial of pegylated liposomal doxorubicin versus bleomycin and vincristine in the treatment of AIDS-related Kaposi's sarcoma. International Pegylated Liposomal Doxorubicin Study Group. J Clin Oncol 16, 683-691.

Suter, B., Auerbach, D., and Stagljar, I.(2006). Yeast-based functional genomics and proteomics technologies: the first 15 years and beyond. Biotechniques 40:625-44.

Thomas, M. B., and Zhu, A. X. (2005) Hepatocellular carcinoma: the need for progress. J Clin Oncol 23, 2892-2899.

Tseng YL, Hong RL, Tao MH, Chang FH. (1999). Sterically stabilized anti-idiotype immunoliposomes improve the therapeutic efficacy of doxorubicin in a murine B-cell lymphoma model. Int J Cancer. 80:723-30.

USP and NF Excipients, Listed by Categories, p. 2404-2406, USP 24 NF 19, United States Pharmacopeial Convention Inc., Rockville, Md. (ISBN 1-889788-03-1), 2000.

Valle, J. W., Dangoor, A., Beech, J., Sherlock, D. J., Lee, S. M., Scarffe, J. H., Swindell, R., and Ranson, M. (2005) Treatment of inoperable hepatocellular carcinoma with pegylated liposomal doxorubicin (PLD): results of a phase II study. Br J Cancer 92, 628-630.

Vasey, P. A., Kaye, S. B., Morrison, R., Twelves, C., Wilson, P., Duncan, R., Thomson, A. H., Murray, L. S., Hilditch, T. E., Murray, T., Burtles, S., Fraier, D., Frigerio, E., and Cassidy, J. (1999) Phase I clinical and pharmacokinetic study of PK1 [N-(2-hydroxypropyl)methacrylamide copolymer doxorubicin]: first member of a new class of chemotherapeutic agents-drug-polymer conjugates. Cancer Research Campaign Phase I/II Committee. Clin Cancer Res 5, 83-94.

Ward et al. (1989) Binding activities of a repertoire of single immunoglobulin variable domains secreted from *Escherichia coli*. Nature 341:544-546.

Willett, C. G., Boucher, Y., di Tomaso, E., Duda, D. G., Munn, L. L., Tong, R. T., Chung, D. C., Sahani, D. V., Kalva, S. P., Kozin, S. V., Mino, M., Cohen, K. S., Scadden, D. T., Hartford, A. C., Fischman, A. J., Clark, W., Ryan, D. P., Zhu, A. X., Blaszkowsky, L. S., Chen, H. X., Shellito, P. C., Lauwers, G. Y., and Jain, R. K. (2004) Direct evidence that the VEGF-specific antibody bevacizumab has antivascular effects in human rectal cancer. Nat Med 10, 145-147.

Wu, H. C., Chang, D. K., and Huang, C. T. (2006) Targeted therapy for cancer. J Cancer Mol 2, 57-66.

Wu, H. C., Jung, M. Y., Chiu, C. Y., Chao, T. T., Lai, S. C., Jan, J. T., and Shaio, M. F. (2003) Identification of a dengue virus type 2 (DEN-2) serotype-specific B-cell epitope and detection of DEN-2-immunized animal serum samples using an epitope-based peptide antigen. The Journal of general virology 84, 2771-2779.

Xiong, X. B., Huang, Y., Lu, W. L., Zhang, X., Zhang, H., Nagai, T., and Zhang, Q. (2005) Enhanced intracellular delivery and improved antitumor efficacy of doxorubicin by sterically stabilized liposomes modified with a synthetic RGD mimetic. J Control Release 107, 262-275.

Zalipsky, S. (1995) Functionalized poly(ethylene glycol) for preparation of biologically relevant conjugates. Bioconjugate Chem., 6:150-165.

Zervos A.S., Gyuris, J., and Brent, R. (1993). Mxi1, a protein that specifically interacts with Max to bind Myc-Max recognition sites. Cell. 72(2):223-32.

Zitzmann, S., Mier, W., Schad, A., Kinscherf, R., Askoxylakis, V., Kramer, S., Altmann, A., Eisenhut, M., and Haberkorn, U. (2005) A new prostate carcinoma binding peptide (DUP-1) for tumor imaging and therapy. Clin Cancer Res 11, 139-146.

* cited by examiner

_US 8,541,543 B2_

SEQUENCE LISTING

<160> NUMBER OF SEQ ID NOS: 35

<210> SEQ ID NO 1
<211> LENGTH: 36

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
agtttttcga ttattcatac gcctattctg ccgctg                                 36

<210> SEQ ID NO 2
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Ser Phe Ser Ile Ile His Thr Pro Ile Leu Pro Leu
1               5                   10

<210> SEQ ID NO 3
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
gagttgatga atcctctttt gccgtttatt cagccg                                 36

<210> SEQ ID NO 4
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Leu Met Asn Pro Leu Leu Pro Phe Ile Gln Pro
1               5                   10

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tcgtttcggc ttgcgactcc tgagtcttcg cgtgtt                                 36

<210> SEQ ID NO 6
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

His Leu Pro Ser Thr Gly Asn Gln Tyr Leu Ser Leu
1               5                   10

<210> SEQ ID NO 7
```

```
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gagactaatt ggactcatag gcctccgctg cgggtg                                36

<210> SEQ ID NO 8
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Glu Thr Asn Trp Thr His Arg Pro Pro Leu Arg Val
1               5                   10

<210> SEQ ID NO 9
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9
gagtatcgta tggcgcatct gactccgtct ttgctg                                36

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Glu Tyr Arg Met Ala His Leu Thr Pro Ser Leu Leu
1               5                   10

<210> SEQ ID NO 11
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tatcatctgc aggattctta gactctgtct ctgctt                                36

<210> SEQ ID NO 12
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Tyr His Leu Gln Asp Ser Glu Thr Leu Ser Leu Leu
1               5                   10
```

```
<210> SEQ ID NO 13
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
tctccttggt atatgactcc tagtcctaat acggcg                              36

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

Ser Pro Trp Tyr Met Thr Pro Ser Pro Asn Thr Ala
1               5                   10

<210> SEQ ID NO 15
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tctgtttctg tgggtatgaa gccgagtcct aggcct                              36

<210> SEQ ID NO 16
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ser Val Ser Val Gly Met Lys Pro Ser Pro Arg Pro
1               5                   10

<210> SEQ ID NO 17
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
gatcctatga cttggacgcc tagtagtgtt atgcgt                              36

<210> SEQ ID NO 18
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Asp Pro Met Thr Trp Thr Pro Ser Ser Val Met Arg
1               5                   10
```

```
<210> SEQ ID NO 19
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19
actcctcatc gtctggattg gtctccgcat ctggtg                             36

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 20

Thr Pro His Arg Leu Asp Trp Ser Pro His Leu Val
1               5                  10

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 21
gggtcgaatc cttggaatac ttggctgact acgctt                             36

<210> SEQ ID NO 22
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Gly Ser Asn Pro Trp Asn Thr Trp Leu Thr Thr Leu
1               5                  10

<210> SEQ ID NO 23
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
aatccgttta atcagcatct gcatgctcag catcct                             36

<210> SEQ ID NO 24
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

Asn Pro Phe Asn Gln His Leu His Ala Gln His Pro
1               5                  10
```

<210> SEQ ID NO 25
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 25
agtgagagta aggatcctac tctttggtat cctgcg         36

<210> SEQ ID NO 26
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 26

Ser Glu Ser Lys Asp Pro Thr Leu Trp Tyr Pro Ala
1               5                   10

<210> SEQ ID NO 27
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 27
tcgtttcggc ttgcgactcc tgagtcttcg cgtgtt         36

<210> SEQ ID NO 28
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 28

Ser Phe Arg Leu Ala Thr Pro Glu Ser Ser Arg Val
1               5                   10

<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 29
ctgcccagta taacgcagca tcggctcatt attcga         36

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 30

Ser Asn Asn Glu Pro Met Leu Arg Tyr Thr Gly Gln

<210> SEQ ID NO 31
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
ccctcatagt tagcgtaacg                                              20

<210> SEQ ID NO 32
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Phe Pro Trp Phe Pro Leu Pro Ser Pro Tyr Gly Asn
1               5                   10

<210> SEQ ID NO 33
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (2)..(2)
<223> OTHER INFORMATION: Xaa = Ile or Leu

<400> SEQUENCE: 33

Pro Xaa Leu Pro
1

<210> SEQ ID NO 34
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Pro Ile Leu Pro
1

<210> SEQ ID NO 35
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

Pro Leu Leu Pro
1

PEPTIDES SPECIFIC FOR HEPATOCELLULAR CARCINOMA CELLS AND APPLICATIONS THEREOF

PRIORITY CLAIM

This application claims priority to provisional application 60/996,488, filed Nov. 20, 2007, which is incorporated by reference in its entirety.

BACKGROUND OF THE INVENTION

On a worldwide basis, hepatocellular carcinoma (HCC) is the tenth most deadly cancer-related killer. Even with the advancement and combination of surgery, radiation and chemotherapy, the prognosis for HCC remains poor (1). The 5-year survival rate for individuals with liver cancer in the United States is only 8.9% despite aggressive conventional therapy, marking this malignancy the second most lethal cancer after pancreatic ductal adenocarcinoma (4.4% survival at 5 years) (2). In 2005, there were over 667,000 new cases of liver cancer worldwide with 80% in Asia and sub-Saharan Africa (3). With tremendous progress in the field of molecular oncology, novel treatment strategies are constantly being developed in attempts to cure this disease.

The development of targeted therapeutics against cancer, with improved discrimination between tumor cells and non-malignant counterparts, is one of the major goals of current anticancer research. Most chemotherapeutic agents do not preferentially accumulate at the tumor sites. Indeed, the dose that reaches the tumor may be as little as 5%-10% of the dose accumulating in normal organs (4). The toxic side effects often limit dose escalation of anticancer drugs, leading to incomplete tumor response, early disease relapse, and ultimately, the development of drug resistance. Several approaches were developed to improve the selective toxicity of anticancer drugs such as encapsulating anticancer drugs in delivery systems (5) and targeting anticancer drugs via monoclonal antibodies (6, 7) or peptide ligands (8, 9) that bind to antigens or receptors that are over-expressed, or uniquely expressed on the cancer cells.

Drug delivery systems (DDS) such as lipid or polymer based anti-cancer nano-medicines have been investigated (10). DDS usually refers to nanoparticles and microparticles with diameters of 200 nm or less including liposomes and other lipid based carriers such as micelles, lipid emulsions, and lipid-drug complexes; also included are polymer-drug conjugates and various ligand targeted products such as immunoconjugates (11). The hyper-permeability of tumor vasculature is one of the key factors governing the successful targeting of a tumor by polymer-based cancer therapies (12). After intravenous administration, the 'leakiness' of the angiogenic tumor vasculature, estimated to have an average pore size of 100-600 nm (13), allows selective extravasation of the conjugate in the tumor tissue. Additionally, tumor tissue frequently lacks effective lymphatic drainage, which subsequently promotes polymer retention. The combination of these factors leads to an accumulation of the conjugate in tumor tissue—a passive targeting phenomenon named by Maeda as the 'enhanced permeability and retention (EPR) effect' (14). EPR-mediated passive tumor targeting by liposomes can result in several-fold increases of drug concentration in solid tumors relative to those obtained with free drugs (15).

The particular strength of DDS is their potential to alter the pharmacokinetics and the biodistribution of their associated therapeutics (5). Coupling of polyethylene glycol (PEG) or other inert polymers to a variety of therapeutic molecules may decrease drug clearance by the kidneys and by the reticular endothelial system (RES) (16). For larger particulate carriers, such as liposomes and polymer-drug conjugates, the size of the carrier (generally 50 to 200 nm in diameter) confines it mainly to the blood compartment, with less pernicious effects on normal organs.

The majority of the DDS currently approved for parenteral administrations include liposomal or lipid based formulations and therapeutic molecules linked to PEG, for instance, PEGylated liposomal doxorubicin, which was used to treat highly angiogenic tumors such as AIDS-related Kaposi's sarcoma, with overall response rates of 43% and 59% (17, 18). However, particulate DDS cause increased accumulation of drugs in mononuclear phagocytic system cells in the liver, spleen, and bone marrow, and the possibility exists for increased toxicities to these tissues (19). Moreover, with the increased circulation time and confinement of the particulate DDS, hematological toxicities such as neutropenia, thrombocytopenia, and leucopenia have also become apparent (20). Efforts are being made to enhance the site-specific actions of DDS by combining them with ligands targeted to tumor cells and tumor vasculature surface antigens or receptors, a process called active- or ligand-mediated targeting (8, 21). In addition, the delivery of chemotherapeutic drugs to tumor tissue through affinity targeting is being investigated (22, 23).

Although monoclonal antibodies have shown clinical potential as tumor targeting agents, poor tumor penetration of the antibodies due to their size, and liver/bone marrow toxicity caused by non-specific antibody uptake are the two major limitations of antibody therapy. Peptide-targeting agents may ease the problems associated with antibody cancer therapy (24). Combinatorial libraries displayed on microorganisms are a possible strategy to identify tumor specific targeting ligands.

Phage display technology has been applied to identify B-cell epitopes (25-27), discover tumor cell (8, 28, 29) and tumor vasculature specific peptides (30-33). Combining DDS with tumor specific peptides may lead to up to several thousand anticancer drug molecules delivered to tumor cells via only a few targeting ligand molecules. The sustained release of the anticancer drug molecules at the tumor site may also have therapeutic advantages (8, 34).

SUMMARY OF THE INVENTION

The present disclosure, inter alia, comprises the following, alone or in combination:

The disclosure provides a polynucleotide, or variants thereof, wherein said polynucleotide encodes a peptide specific for hepatocellular carcinoma cells and said polynucleotide comprises a sequence chosen from SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, and SEQ ID NO: 29.

The disclosure provides a polypeptide, or variants thereof, wherein said polypeptide is specific for hepatocellular carcinoma cells and said polypeptide comprises a sequence chosen from SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, and SEQ ID NO: 30. In one embodiment, the polypeptide comprises SP94 (SEQ ID NO: 2), or a variant thereof. In another embodiment, the polypeptide comprises SP94 (SEQ ID NO: 2). In another embodiment, the polypeptide comprises contiguous amino acids PILP.

The disclosure provides fusion proteins comprising a first polypeptide fused to a second polypeptide, wherein the first polypeptide comprises a polypeptide specific for hepatocellullar carcinoma cells, and a second peptide. In one embodiment, the second polypeptide comprises one or more polypeptides specific for hepatocellullar carcinoma cells (e.g., the polypeptide is a homodimer, heterodimer, or other multimer). In another embodiment, the second polypeptide comprises a glutathione S-transferase (GST) domain. In another embodiment, the second polypeptide comprises GFP. In another embodiment, the second polypeptide comprises an immunological tag. In another embodiment, the second polypeptide comprises an antibody domain. In another embodiment, the antibody domain is the Fc region of an antibody.

The disclosure provides polypeptides or variants thereof, wherein said polypeptides are specific for hepatocellular carcinoma cells and, wherein the polypeptides, or variants, thereof are conjugated to one or more drugs. In one embodiment, the drugs are chosen from doxorubicin, vinorelbine, vincristine, paclitaxel, lurotecan, an oligonucleotide, a toxin, an anti-VEGF aptamer, and a radioactive molecule.

The disclosure provides antibodies that bind polypeptides, or variants thereof, that are specific for hepatocellular carcinoma cells.

The disclosure provides liposomes comprising a polypeptide, or variant thereof, specific for hepatocellular carcinoma cells In one embodiment, the liposome comprises SP94 (SEQ ID NO: 2), or a variant thereof. In another embodiment, the liposome comprises SP94 (SEQ ID NO: 2). In another embodiment, a liposome of the disclosure further comprises at least one drug chosen from doxorubicin, vinorelbine, vincristine, paclitaxel, lurotecan, an oligonucleotide, a toxin, an anti-VEGF aptamer, and a radioactive molecule. In another embodiment, the liposome comprises doxorubicin.

The disclosure provides methods for treating a disease in a mammal comprising administering to a mammal in need of treatment a therapeutically effective amount of a polypeptide, or variant thereof, specific for hepatocellular carcinoma cells, wherein the polypeptide, or variant thereof, is conjugated to one or more drugs chosen from doxorubicin, vinorelbine, vincristine, paclitaxel, lurotecan, an oligonucleotide, a toxin, an anti-VEGF aptamer, and a radioactive molecule. In one embodiment, the mammal is human.

The disclosure provides methods of treating a disease in a mammal comprising administering to a mammal in need of treatment a therapeutically effective amount of a liposome comprising one or more drugs and a polypeptide, or variants thereof, specific for hepatocellular carcinoma cells. In one embodiment, the liposome comprises a polypeptide comprising SEQ ID NO: 2, or a variant thereof. In another embodiment, the liposome comprises a polypeptide comprising SEQ ID NO: 2. In another embodiment, the liposome comprises one or more drugs including doxorubicin, vinorelbine, vincristine, paclitaxel, lurotecan, an oligonucleotide, a toxin, an anti-VEGF aptamer, and a radioactive molecule. In one embodiment, the liposome comprises doxorubicin. In another embodiment the liposome comprises SEQ ID NO: 2, or a variant thereof, and doxorubicin. In another embodiment, the liposome comprises SEQ ID NO: 2 and doxorubicin. In another embodiment, the disease is cancer. In another embodiment, the cancer is liver cancer. In another embodiment, the liver cancer is hepatocellular carcinoma. In another embodiment, the mammal is a human.

The disclosure provides methods for detecting liver cancer in a specimen comprising: a) contacting the specimen with a polypeptide, or variants thereof, specific for hepatocellular carcinoma cells under conditions that allow binding of the polypeptide with liver cancer cells; and b) detecting the binding of the polypeptide using an antibody that binds the polypeptide. In one embodiment, the polypeptide, or variant thereof, comprises a fusion polypeptide comprising a polypeptide specific for hepatocellular carcinoma and another sequence comprising an epitope. Binding of the fusion polypeptide to hepatocellular carcinoma cells may be detected using an antibody that binds to the epitope.

The disclosure provides methods of identifying cellular molecules that bind to a polypeptide, or variant thereof, specific for hepatocellular carcinoma cells comprising: a) contacting a cellular extract with the polypeptide, or variant thereof, under conditions that allow formation of a complex comprising the polypeptide, or variant thereof, and the molecule; and b) analyzing the complex to identify the cellular molecule. In one embodiment, the cellular molecule resides on the surface of a hepatocellular carcinoma cell and binds the polypeptide, or variant thereof.

The disclosure provides a variant of a polynucleotide of the disclosure, wherein the variant polynucleotide hybridizes to the complement of a polynucleotide chosen from SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, and SEQ ID NO: 29. In one embodiment, the polynucleotide hybridizes under stringent conditions.

The disclosure provides a variant of polypeptide of the disclosure, wherein the variant polypeptide is encoded by polynucleotide that hybridizes to the complement of a polynucleotide chosen from SEQ ID NO: 1, SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, and SEQ ID NO: 29. In one embodiment, the polynucleotide hybridizes under stringent conditions.

The disclosure provides a method for detecting cancer in a subject comprising administering to the subject a polypeptide of the disclosure, wherein said polypeptide comprises a label, and detecting binding of the polypeptide to cancer in the subject. In one embodiment, the label comprises a radioactive molecule. In another embodiment, the cancer is liver cancer. In another embodiment, the liver cancer is hepatocellular carcinoma. In another embodiment, the subject is a mammal. In another embodiment, the mammal is a human.

BRIEF DESCRIPTION OF THE FIGURES AND TABLES

The patent or application file contains at least one drawing executed in color. Copies of the patent or patent application publication with color drawing(s) will be provided by the Office upon request and payment of the necessary fee.

FIG. 1. Isolation of HCC cell-specific phages using in vitro phage display.

FIGS. 2A-D. The binding activity of PC94 to HCC cell lines and human HCC biopsy specimens.

Figure 3B:
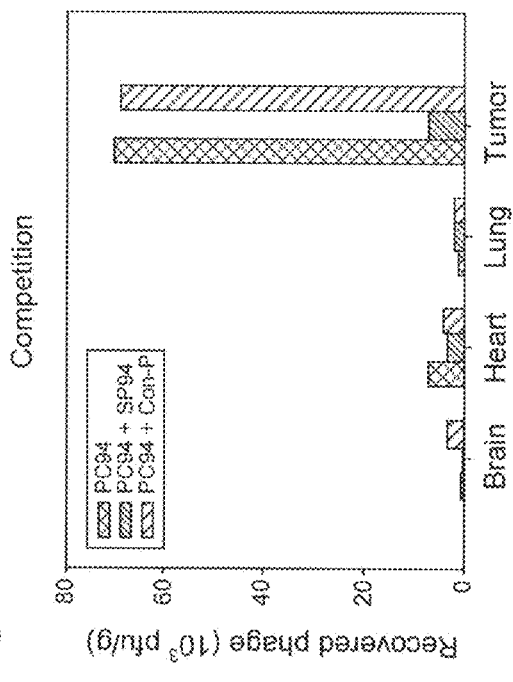
Figure 3A:
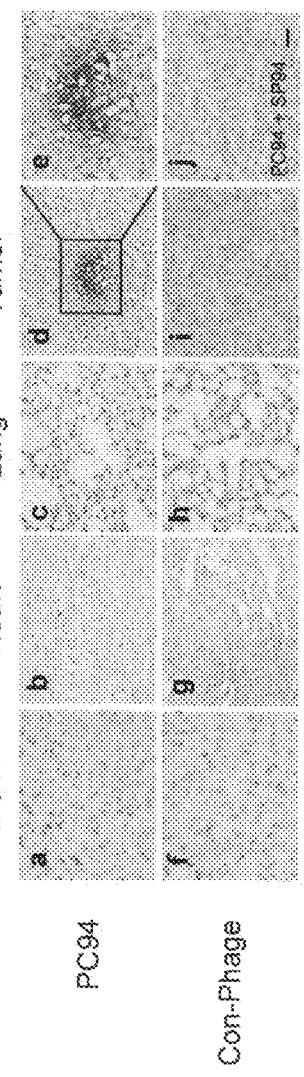
Figure 3C:
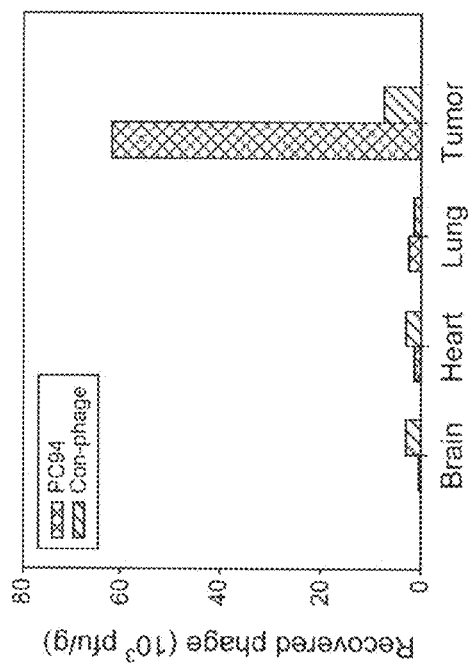

FIGS. 3A-C. Verification of tumor homing ability of PC94 in vivo.

FIGS. 4A-D. Conjugation of targeting peptide SP94 enhances the therapeutic efficacy and reduces the hematological toxicity of liposomal doxorubicin in the HCC xenograft model.

FIGS. 5A-D. Histopathological examination of SP94-Lipo-Dox treated HCC xenografts.

FIGS. 6A-E. Treatment of SCID mice bearing large HCC xenografts with SP94-Lipo-Dox.

Figure 7:
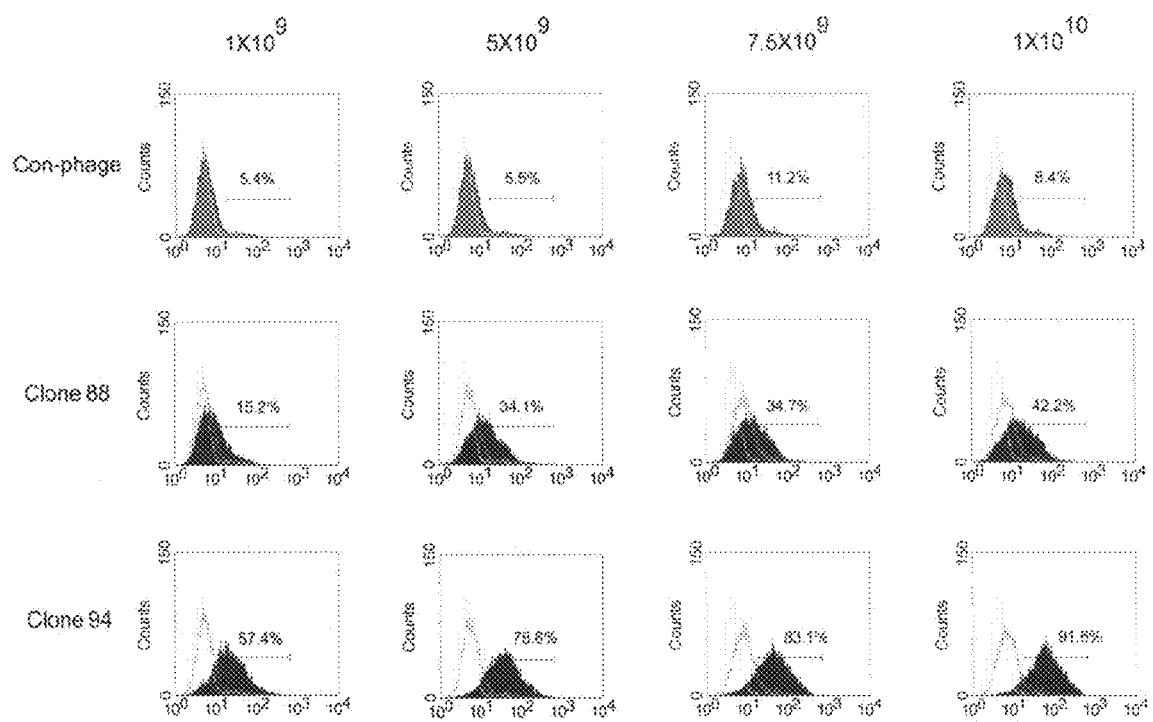

FIG. 7. Dose dependent analysis of the binding activity of the selected phage clones by FACS.

Figure 8:
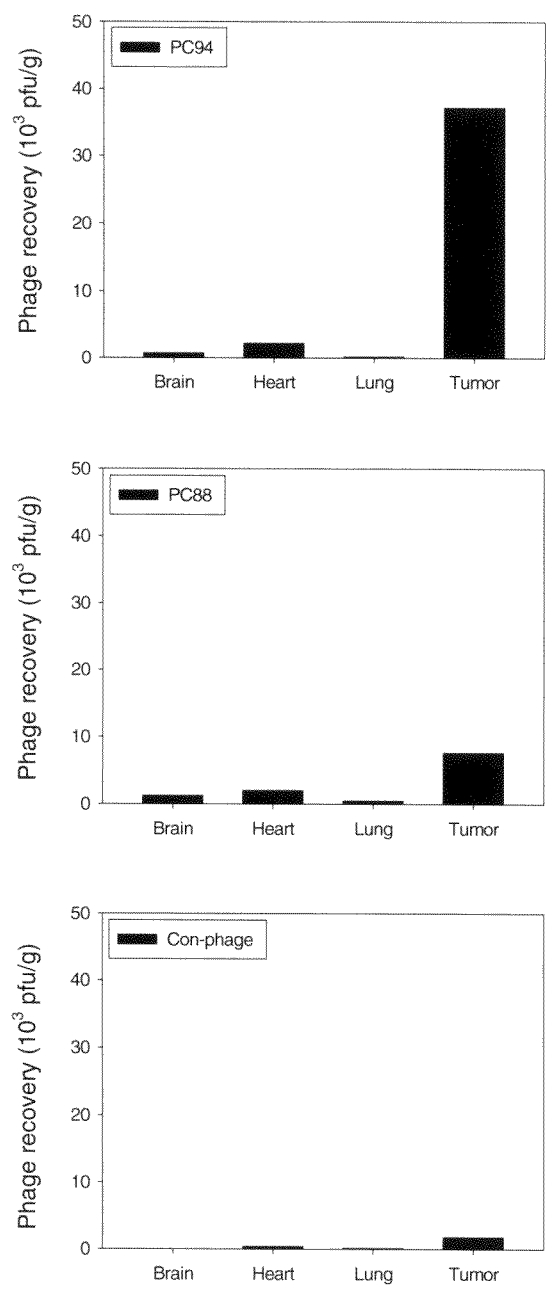

FIG. 8. Verification of tumor homing ability of PC88 and 94 in vivo.

Table 1 provides phage-displayed polypeptide sequences from phage selected from Mahlavu cells.

Table 2 provides polynucleotide sequences encoding polypeptides of the disclosure.

DETAILED DESCRIPTION OF THE INVENTION

HCC is the fifth most common cancer and ranks as the fourth leading cause of cancer death worldwide (1). The only curative treatments are surgical resection or liver transplantation, and only a few patients are eligible for these procedures (36). The majority of HCCs that present at an advanced stage are beyond curative treatment. Systemic chemotherapy against advanced HCCs, either as single agent therapy or in combination, has been investigated extensively in the past 30 years and is widely regarded as ineffective (36). Improving the effectiveness of systemic treatment and selecting those patients who would benefit remains a major challenge. We report novel targeting peptides identified via phage display screening, polypeptides specific for hepatocellular carcinoma cells, and the development of targeted drug delivery against HCC using the peptides.

Initially, we used a phage-displayed peptide library to identify novel peptides, which can specifically bind to HCC cells both in vitro and in vivo. One such peptide is SP94. In addition, PC94, the phage encoding SP94, recognized the tumor tissue surface but not normal counterparts in surgical specimens from HCC patients. Conjugation of the targeting peptide SP94 and liposomes containing doxorubicin improved therapeutic efficacy in an HCC xenograft model. The SP94 peptide thus can improve the systemic treatment of advanced HCCs.

I. DEFINITIONS

The terms used herein have their ordinary meanings, as set forth below, and can be further understood in the context of the specification.

The terms "polynucleotide, "nucleotide," "nucleic acid," "nucleic acid molecule," "nucleic acid sequence," "polynucleotide sequence," and "nucleotide sequence" are used interchangeably herein to refer to polymeric forms of nucleotides of any length. The polynucleotides can comprise deoxyribonucleotides, ribonucleotides, and/or their analogs or derivatives. Nucleotide sequences shown herein are listed in the 5' to 3' direction.

The terms "polypeptide," "peptide," and "protein," are used interchangeably herein, refer to a polymeric form of amino acids of any length.

The term "variants" include insertions, additions, deletions, or substitutions in a polynucleotide or polypeptide sequences of the disclosure, wherein said variant is specific for hepatocellular carcinoma cells.

The phrase "substantially identical", "substantially similar" or means that the relevant amino acid or nucleotide sequence will be identical to or have insubstantial differences (through conserved amino acid substitutions) in comparison to the sequences which are disclosed.

For polypeptides, at least 10, 20, 30, 50, 100, or more amino acids will be compared between the original polypeptide and the variant polypeptide that is substantially identical to the original. For nucleic acids, at least 30, 40, 50, 100, 150, 300 or more nucleotides will be compared between the original nucleic acid and the variant nucleic acid that is substantially identical to the original. Thus, a variant could be substantially identical in a region or regions, but divergent in others, while still meeting the definition of "substantially identical." Percent identity between two sequences is determined by standard alignment algorithms such as, for example, Basic Local Alignment Tool (BLAST) described in Altschul et al., J. Mol. Biol., 215:403-410 (1990), the algorithm of Needleman et al., J. Mol. Biol., 48:444-453 (1970), or the algorithm of Meyers et al., Comput. Appl. Biosci., 4:11-17 (1988).

The term "liposome" refers to a composition comprising an outer lipid bi-layer or multi-layer membrane surrounding an internal aqueous space. The term includes multilamellar liposomes, which generally have a diameter in the range of about one to about ten micrometers and comprise anywhere from two to hundreds of concentric lipid bilayers alternating with layers of an aqueous phase. The term includes unilamellar vesicles which are comprised of a single lipid layer and generally have a diameter in the range of about 20 to about 400 nanometers (nm), about 50 to about 300 nm, about 300 to about 400 nm, or about 100 to about 200 nm. The term also includes liposomes with diameters from about 65 nm to about 75 nm.

The term "antibody" refers to an immunoglobulin or fragment thereof, and encompasses any polypeptide comprising an antigen-binding fragment or an antigen-binding domain. The term includes but is not limited to polyclonal, monoclonal, monospecific, polyspecific, non-specific, humanized, human, single-chain, chimeric, synthetic, recombinant, hybrid, mutated, grafted, and in vitro generated antibodies. Unless preceded by the word "intact", the term "antibody" includes antibody fragments such as Fab, F(ab')$_2$, Fv, scFv, Fd, dAb, and other antibody fragments that retain antigen-binding function. Typically, such fragments would comprise an antigen-binding domain.

The terms "antigen-binding domain" and "antigen-binding fragment" refer to a part of an antibody molecule that comprises amino acids responsible for the specific binding between antibody and antigen. The part of the antigen that is specifically recognized and bound by the antibody is referred to as the "epitope," which may or may not be a contiguous sequence of amino acid residues in a polypeptide, and which may comprise sugars and/or molecules having other chemical structures. An antigen-binding domain may comprise an antibody light chain variable region ($V_L$) and an antibody heavy chain variable region ($V_H$); however, it does not have to comprise both. Fd fragments, for example, have two $V_H$ regions and often retain some antigen-binding function of the intact antigen-binding domain. Examples of antigen-binding fragments of an antibody include (1) a Fab fragment, a monovalent fragment having the $V_L$, $V_H$, $C_L$ and $C_H1$ domains; (2) a F(ab')$_2$ fragment, a bivalent fragment having two Fab fragments linked by a disulfide bridge at the hinge region; (3) a Fd fragment having the two $V_H$ and $C_H1$ domains; (4) a Fv fragment having the $V_L$ and $V_H$ domains of a single arm of an antibody, (5) a dAb fragment (Ward et al., (1989) Nature 341:544-546), which has a $V_H$ domain; and (6) an isolated complementarity determining region (CDR). Furthermore, although the two domains of the Fv fragment, $V_L$ and $V_H$, are coded for by separate genes, they can be joined, using recombinant methods, by a synthetic linker that enables them to be made as a single protein chain in which the $V_L$ and $V_H$ regions pair to form monovalent molecules (known as single chain Fv (scFv); see e.g., Bird et al. (1988) Science 242:423-426; and Huston et al. (1988) Proc. Natl. Acad. Sci. USA 85:5879-5883). These antibody fragments are obtained using conventional techniques known to those with skill in the art, and the fragments are screened for utility in the same manner as are intact antibodies.

The term "hybridizes specifically," in the context of a polynucleotide, refers to hybridization under stringent conditions. Conditions that increase stringency of both DNA/DNA and DNA/RNA hybridization reactions are widely known and published in the art. Examples of stringent hybridization conditions include hybridization in 4× sodium chloride/sodium citrate (SSC), at about 65-70° C., or hybridization in 4×SSC plus 50% formamide at about 42-50° C., followed by one or more washes in 1×SSC, at about 65-70° C.

A peptide is "specific for" hepatocellular carcinoma cells when the peptide binds to or interacts with hepatocellular carcinoma cells but does not bind to or interact significantly with other cells.

The term "ligand" refers to a molecule that binds to another molecule, including a receptor.

A "host cell" is an individual cell or cell culture which can be or has been a recipient of any recombinant vector(s) or isolated polynucleotide. Host cells include progeny of a single host cell, and the progeny may not necessarily be completely identical (in morphology or in total DNA complement) to the original parent cell due to natural, accidental, or deliberate mutation and/or change. A host cell includes cells transfected or infected in vivo or in vitro with a recombinant vector or a polynucleotide of the disclosure. A host cell which comprises a recombinant vector of the disclosure may be called a "recombinant host cell."

A "specimen" is any biological specimen derived from a patient. The term includes, but is not limited to, biological fluids such as blood, serum, plasma, urine, cerebrospinal fluid, tears, saliva, lymph, dialysis fluid, lavage fluid, semen, and other liquid samples, as well as cell and tissues of biological origin. The term also includes cells or cells derived therefrom and the progeny thereof, including cells in culture, cell supernatants, and cell lysates. It further includes organ or tissue culture-derived fluids, tissue biopsy samples, tumor biopsy samples, stool samples, and fluids extracted from physiological tissues, as well as cells dissociated from solid tissues, tissue sections, and cell lysates. This definition encompasses samples that have been manipulated in any way after their procurement, such as by treatment with reagents, solubilization; or enrichment for certain components, such as polynucleotides or polypeptides. Also included in the term are derivatives and fractions of patient samples. A patient sample may be used in a diagnostic, prognostic, or other monitoring assay. The term also applies to a biological specimen from a non-human mammal. The specimen can be from a human patient or a non-human mammal.

"Treatment," as used herein, covers any administration or application of remedies for disease in a mammal, including a human, and includes inhibiting the disease, arresting its development, or relieving the disease, for example, by causing regression, or restoring or repairing a lost, missing, or defective function, or stimulating an inefficient process. The term includes obtaining a desired pharmacologic and/or physiologic effect, covering any treatment of a pathological condition or disorder in a mammal, including a human. The effect may be prophylactic in terms of completely or partially preventing a disorder or symptom thereof and/or may be therapeutic in terms of a partial or complete cure for a disorder and/or adverse affect attributable to the disorder. Thus, the disclosure provides both treatment and prophylaxis. It includes (1) preventing the disorder from occurring or recurring in a subject who may be predisposed to the disorder but is not yet symptomatic, (2) inhibiting the disorder, such as arresting its development, (3) stopping or terminating the disorder or at least symptoms associated therewith, so that the host no longer suffers from the disorder or its symptoms, such as causing regression of the disorder or its symptoms, for example, by restoring or repairing a lost, missing or defective function, or stimulating an inefficient process, or (4) relieving, alleviating, or ameliorating the disorder, or symptoms associated therewith, where ameliorating is used in a broad sense to refer to at least a reduction in the magnitude of a parameter, such as inflammation, pain, and/or tumor size.

A "pharmaceutically acceptable carrier" refers to a non-toxic solid, semisolid or liquid filler, diluent, encapsulating material, formulation auxiliary, or excipient of any conventional type. A pharmaceutically acceptable carrier is non-toxic to recipients at the dosages and concentrations employed and is compatible with other ingredients of the formulation.

A "composition" herein refers to a mixture that usually contains a carrier, such as a pharmaceutically acceptable carrier or excipient that is conventional in the art and which is suitable for administration into a subject for therapeutic, diagnostic, or prophylactic purposes. It may include a cell culture in which the polypeptide or polynucleotide is present in the cells or in the culture medium. For example, compositions for oral administration can form solutions, suspensions, tablets, pills, capsules, sustained release formulations, oral rinses, or powders.

"Disease" refers to any condition, infection, disorder, or syndrome that requires medical intervention or for which medical intervention is desirable. Such medical intervention can include treatment, diagnosis, and/or prevention.

"Cancer" is any abnormal cell or tissue growth, for example, a tumor, whether malignant, pre-malignant, or non-malignant. It is characterized by uncontrolled proliferation of cells that may or may not invade the surrounding tissue and, hence, may or may not metastasize to new body sites. Cancer encompasses carcinomas, which are cancers of epithelial cells, carcinomas include squamous cell carcinomas, adenocarcinomas, melanomas, and hepatomas. Cancer also encompasses sarcomas, which are tumors of mesenchymal origin, sarcomas include osteogenic sarcomas, leukemias, and lymphomas. Cancers may involve one or more neoplastic cell type. The term cancer includes lung cancer, colon cancer, breast cancer, prostate cancer, liver cancer, pancreatic cancer, and oral cancer.

II. POLYPEPTIDES OF THE DISCLOSURE SPECIFIC FOR HEPATOCELLULAR CARCINOMA CELLS

The disclosure provides a polynucleotide, or a variant thereof, wherein said polynucleotide encodes a polypeptide specific for hepatocellular carcinoma cells and said polynucleotide comprises a sequence chosen from SEQ ID NO: 1, SEQ ID NO: 3, SEQ ID NO:5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, and SEQ ID NO: 29.

The disclosure provides a polypeptide, or variants thereof, wherein said polypeptide is specific for hepatocellular carcinoma cells and said polypeptide comprises a sequence chosen from SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, and SEQ ID NO: 30. In one embodiment, the polypeptide comprises SP94 (SEQ ID NO: 2), or a variant thereof. In another embodiment, the polypeptide comprises SP94 (SEQ ID NO: 2).

A. Variants

Variants include biologically active variants of the peptides, where include variants that are substantially similar or substantially identical in structure. Variants of peptide sequences may include insertions, additions, deletions, or substitutions compared with the subject peptides. Variants of polypeptide sequences include biologically active polymorphic variants.

Variants of the nucleotides and polypeptides of the disclosure include, for example, those that are at least about 50%, at least about 55%, at least about 60%, at least about 65%, at least about 70%, at least about 75%, at least about 80%, at least about 85%, at least about 90%, at least about 92%, at least about 93%, at least about 94%, at least about 95%, at least about 96%, at least about 97%, at least about 98%, or at least about 99% identical in sequence to nucleic acid molecules and polypeptides disclosed.

Variants of the nucleotides and polypeptides of the disclosure include, for example, those that are at least about 50%, at least about 55%, at least about 60%, at least about 65%, at least about 70%, at least about 75%, at least about 80%, at least about 85%, at least about 90%, at least about 92%, at least about 93%, at least about 94%, at least about 95%, at least about 96%, at least about 97%, at least about 98%, or at least about 99% similar in sequence to nucleic acid molecules and polypeptides disclosed.

Variants of the polypeptides of the disclosure include variants with 1, 2, 3, 4, 5, 6 or more insertions, additions, deletions or substitutions compared with the sequences in Table 1. In one embodiment, the variant comprises 1, 2, 3, 4, 5, 6 or more insertions, additions, deletions or substitutions compared with a sequence provided in Table 1, wherein the insertions, additions, deletions or substitutions do not change the amino acids indicated in bold in Table 1 for that sequence. In another embodiment, the variant comprises the amino acids from a single sequence which are indicated in bold in Table 1.

Variants of the polynucleotides of the disclosure include variants with 1, 2, 3, 4, 5, 6, 7, 8, 9, 10, 11, 12, 13, 14, 15, 16, 17 or 18 insertions, additions, deletions or substitutions compared with the sequences provided in Table 2. In one embodiment, the variant comprises insertions, additions, deletions or substitutions compared with a sequence provided in Table 2, wherein the insertions, additions, deletions or substitutions do not change the nucleotides which encode the amino acids indicated in bold in Table 1 for that sequence. In another embodiment, the variant comprises the nucleotides that encode the amino acids from a single sequence that are indicated in bold in Table 1.

Peptide variants may include coded and non-coded amino acids, chemically or biochemically modified, derivatized, or designer amino acids, amino acid analogs, peptidomimetics, and depsipeptides, and polypeptides having modified, cyclic, bicyclic, depsicyclic, or depsibicyclic peptide backbones. Variants include single chain proteins as well as multimers.

Variants of the peptides of the disclosure can include naturally-occurring and non-naturally occurring amino acids. Variants can comprise D-amino acids, a combination of D- and L-amino acids, and various "designer" or "synthetic" amino acids (for example, β-methyl amino acids, Cα-methyl amino acids, and Nα-methyl amino acids, etc.) to convey special properties. Additionally, variants can be cyclic. Variants can include non-classical amino acids in order to introduce particular conformational motifs. Any known non-classical amino acid can be used. Amino acid analogs and peptidomimetics can be incorporated into a peptide to induce or favor specific secondary structures, including, but not limited to, LL-Acp (LL-3-amino-2-propenidone-6-carboxylic acid), a β-turn inducing dipeptide analog, β-sheet inducing analogs, β-turn inducing analogs, α-helix inducing analogs, γ-turn inducing analogs, Gly-Ala turn analogs, amide bond isostere, or tretrazol, and the like.

A desamino or descarboxy residue can be incorporated at the terminal ends of the variant, so that there is no terminal amino or carboxyl group, to decrease susceptibility to proteases or to restrict conformation. C-terminal functional groups include amide, amide lower alkyl, amide di (lower alkyl), lower alkoxy, hydroxy, and carboxy, and the lower ester derivatives thereof, and the pharmaceutically acceptable salts thereof.

Furthermore, if desired, nonclassical amino acids or chemical amino acid analogs can be introduced as a substitution or addition into the polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

Variants include polynucleotide sequences that are substantially similar to the peptides of the disclosure. Such variants may be encoded by a nucleic acid that hybridizes to the complement of a polynucleotide of the disclosure.

B. Fusion Proteins and Conjugates

The disclosure provides a fusion protein comprising a first polypeptide fused to a second polypeptide, wherein the first polypeptide comprises a polypeptide specific for hepatocellullar carcinoma cells, and a second peptide. The second peptide is chosen from, but not limited to, glutathione S-transferase (GST), a heterologous amino acid sequence such as bioluminescent protein, for example, luciferin, or aequorin (green fluorescent protein), with heterologous and homologous leader sequences. The fusion proteins may comprise N-terminal methionine residues, pegylated proteins, and immunologically tagged, or HIS-tagged proteins. Such fusion proteins also include fusions to epitopes. Such fusion proteins can comprise multimers of the peptides of the disclosure, e.g. homodimers or homomultimers, and heterodimers and heteromultimers.

The peptides of the disclosure may be conjugated to a label such as, but not limited to, FITC, biotin, and radioisotopes, including, but not limited to $^{64}$Cu, $^{67}$Cu, $^{90}$Y, $^{99}$mTc, $^{111}$In, $^{124}$I, $^{125}$I, $^{131}$I, $^{137}$Cs, $^{186}$Re, $^{211}$At, $^{212}$Bi, $^{213}$Bi, $^{223}$Ra$^{241}$Am, and $^{244}$Cm, enzymes having detectable products (for example, luciferase, peroxidase, alkaline phosphatase, β-galactosidase, and the like), fluorescers and fluorescent labels, fluorescence emitting metals, for example, $^{152}$Eu, or others of the lanthanide series, electrochemiluniescent compounds, chemiluminescent compounds, for example, luminol, isoluminol, or acridinium salts, specific binding molecules, for example, magnetic particles, microspheres, nanospheres, and the like. The peptides of the disclosure may be conjugated to therapeutic agents such as vinorelbine, cisplatin, gemcitabine, paclitaxel, etoposide, Novantrone (mitoxantrone), actinomycin D, camptothecin (or water soluble derivatives thereof), methotrexate, mitomycins (for example, mitomycin C), dacarbazine (DTIC), cyclophosphamide, and anti-neoplastic antibiotics such as doxorubicin and daunomycin, or others, described, for example, in (De Vita et al., 2001). Peptides may also be conjugated to cytotoxic drugs, oligonucleotides, toxins and radioactive molecules, or compounds such as anti-VEGF aptamers described in (Ng et al 2006).

III. METHODS OF MAKING THE POLYPEPTIDES SPECIFIC FOR HEPATOCELLULAR CARCINOMA CELLS

The peptides of the disclosure can be produced using methods known in the art. Cell-based methods and cell-free methods are suitable for producing peptides of the disclosure. Cell-based methods generally involve introducing a nucleic acid into a host cell in vitro and culturing the host cell under conditions suitable for expression, then harvesting the peptide, either from the culture medium or from the host cell, for example by disrupting the host cell, or both. Suitable host cells include prokaryotic or eukaryotic cells, including, for example, bacterial, yeast, fungal, plant, insect, and mammalian cells.

The disclosure also provides methods of producing a peptide using cell-free in vitro transcription/translation methods, which are well known in the art.

Typically, a heterologous peptide, whether modified or unmodified, may be expressed on its own, as described above, or as a fusion protein, and may include not only secretion signals, but also a secretory leader sequence. A secretory leader sequence of the disclosure may direct certain proteins to the endoplasmic reticulum (ER). The ER separates the membrane-bound proteins from other proteins. Once localized to the ER, proteins can be further directed to the Golgi apparatus for distribution to vesicles, including secretory vesicles, the plasma membrane, lysosomes, and other organelles.

Additionally, peptide moieties and/or purification tags may be added to the peptides. Such regions may be removed prior to final preparation of the polypeptide. The addition of peptide moieties to polypeptides to engender secretion or excretion, to improve stability, and to facilitate purification, among other reasons, are familiar and routine techniques in the art. Suitable purification tags include, for example, V5, polyhistidines, avidin, and biotin. Conjugation of peptides to compounds such as biotin can be accomplished using techniques well known in the art. (Hermanson ed. (1996) Bioconjugate Techniques; Academic Press). Peptides can also be conjugated with radioisotopes, toxins, enzymes, fluorescent labels, colloidal gold, nucleic acids, vinorelbine, and doxorubicin using techniques known in the art. (Hermanson ed. (1996) Bioconjugate Techniques; Academic Press; Stefano et al. (2006). Toxins include immunotoxins. Kreitman and Pastan, Immunotoxins in the treatment of hematologic malignancies. Curr Drug Targets. 7:1301-11 (2006).

Fusion partners suitable for use in the disclosure include, for example, fetuin, human serum albumin, Fc, and/or one or more of their fragments. Conjugated proteins, such as polyethylene glycol conjugates, are also provided.

The peptides of the disclosure can also be chemically synthesized using techniques known in the art (e.g., see Hunkapiller et al., Nature, 310:105 111 (1984); Grant ed. (1992) Synthetic Peptides, A Users Guide, W.H. Freeman and Co.; U.S. Pat. No. 6,974,884)). For example, a polypeptide corresponding to a fragment of a polypeptide can be synthesized by use of a peptide synthesizer or through the use of solid-phase methods known in the art.

The polypeptides of the disclosure can be recovered and purified from chemical synthesis and recombinant cell cultures by standard methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding protein may be employed to regenerate active conformation when the polypeptide is denatured during isolation and/or purification.

A peptide or peptidomimetic of the disclosure can be modified with or covalently coupled to one or more of a variety of hydrophilic polymers to increase solubility and circulation half-life of the peptide. Suitable nonproteinaceous hydrophilic polymers for coupling to a peptide include, but are not limited to, polyalkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran, and dextran derivatives. Generally, such hydrophilic polymers have an average molecular weight ranging from about 500 to about 100,000 daltons, from about 2,000 to about 40,000 daltons, or from about 5,000 to about 20,000 daltons. The peptide can be derivatized with or coupled to such polymers using any of the methods set forth in Zallipsky, S. (1995) Bioconjugate Chem., 6:150-165; Monfardini, C., et al. (1995) Bioconjugate Chem. 6:62-69; U.S. Pat. Nos. 4,640,835; 4,496,689; 4,301,144; 4,670,417; 4,791,192; 4,179,337, or WO 95/34326.

IV. GENERATION OF ANTIBODIES

Isolated proteins of the present disclosure may be used to generate antibodies, either monoclonal or polyclonal, using methods of antibody production that are generally known in the art. Thus, the present disclosure also includes antibodies to peptides specific for hepatocellular carcinoma cells. The antibodies include both antibodies that block activity and antibodies that do not.

Antibodies can be made, for example, via traditional hybridoma techniques (Kohler and Milstein, Nature 256:495-499 (1975)), recombinant DNA methods (for example, U.S. Pat. No. 4,816,567), or phage display techniques using antibody libraries (Clackson et al., Nature 352: 624-628 (1991); Marks et al., J. Mol. Biol. 222:581-597 (1991)). For various antibody production techniques, see Antibodies: A Laboratory Manual, eds. Harlow et al., Cold Spring Harbor Laboratory (1988).

Antibodies of the disclosure may be used in the treatment of the diseases described below. Antibodies can also be used in the assays and methods of detection described.

V. PREPARATION OF LIPOSOMES

A variety of methods for preparing liposomes are known in the art, several of which are described by Lichtenberg and Barenholz in Methods of Biochemical Analysis, Volume 33, 337-462 (1988). Small unilamellar vesicles (SUV, size <100 nm) can be prepared by a combination of standard methods of thin-film hydration and repeated extrusion as described before (Tseng et al., 1999). Preparation methods particularly involving the encapsulation of DNA by liposomes, and methods that have a direct application to liposome-mediated transfection, have been described by Hug and Sleight et al (1991). Methods of making liposomes are also disclosed in U.S. Pat. No. 6,355,267 and U.S. Pat. No. 6,663,885. Liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter.

Liposomes are also commercially available from sources such as the Taiwan Liposome Company, Taipei Taiwan. Additional commercially available liposomes include TLC-D99, Lipo-Dox, Doxil, DaunoXome, AmBisome, ABELCET, transfectace (DDAB/DOPE), DOTAP/DOPE and Lipofectin.

The liposomes of the present disclosure are most frequently prepared from phospholipids, but other molecules of similar molecular shape and dimensions having both a hydrophobic and a hydrophilic moiety can be used. For the purposes of the present disclosure, all such suitable liposome-forming molecules will be referred to herein as lipids. One or more naturally occurring and/or synthetic lipid compounds may be used in the preparation of the liposomes.

Liposomes may be anionic, cationic or neutral depending upon the choice of the hydrophilic group. For instance, when a compound with a phosphate or a sulfate group is used, the resulting liposomes will be anionic. When amino-containing lipids are used, the liposomes will have a positive charge, and will be cationic liposomes.

Representative suitable phospholipids or lipid compounds for forming initial liposomes useful in the present disclosure include, but are not limited to, phospholipid-related materials such as phosphatidylcholine (lecithin), lysolecithin, lysophosphatidylethanol-amine, phosphatidylserine, phosphatidylinositol, sphingomyelin, phosphatidylethanolamine (cephalin), cardiolipin, phosphatidic acid, cerebrosides, dicetylphosphate, phosphatidylcholine, and dipalmitoyl-phosphatidylglycerol. Additional nonphosphorous-containing lipids include, but are not limited to, stearylamine, dodecylamine, hexadecyl-amine, acetyl palmitate, glycerol ricinoleate, hexadecyl sterate, isopropyl myristate, amphoteric acrylic polymers, fatty acid, fatty acid amides, cholesterol, cholesterol ester, diacylglycerol, diacylglycerolsuccinate, and the like.

Liposomal preparations for use in the instant disclosure include cationic (positively charged), anionic (negatively charged), and neutral preparations.

Remote loading of compounds into liposomes employs formation of transmembrane gradients (Ceh and Lasic, 1995). This method includes incubating the compound to be loaded into the liposomes and a boronic acid compound with suspended liposomes, thereby achieving accumulation of the compound within the liposomes (Zalipsky et al., 1998; Ceh B. and Lasic D. D., 1995; Zalipsky et al 1998; U.S. Pat. No. 6,051,251).

A phosphate assay can be used to determine liposome concentration. One phosphate assay is based on the interaction between molybdate and malachite green dye. The main principle involves the reaction of inorganic phosphate with molybdate to form a colorless unreduced phosphomolybdate complex which is converted to a blue colored complex when reduced under acidic conditions. Phosphomolybdate gives 20 or 30 times more color when complexed with malachite green. The final product, reduced green soluble complex is measured by its absorbance at 620 nm and is a direct measure of inorganic phosphate in solution.

VI. PREPARATION OF PHARMACEUTICAL COMPOSITIONS

The liposomes, peptides, and antibodies of the disclosure may comprise one or more of the wide variety of drugs that have been employed in cancer treatment and inhibition of angiogenesis, including, but are not limited to, vinorelbine, cisplatin, gemcitabine, paclitaxel, etoposide, Novantrone (mitoxantrone), actinomycin D, camptohecin (or water soluble derivatives thereof), methotrexate, mitomycins (for example, mitomycin C), dacarbazine (DTIC), cyclophosphamide, and anti-neoplastic antibiotics such as doxorubicin and daunomycin, or others, described, for example, in (De Vita et al., 2001). The liposomes, peptides, and antibodies can also comprise cytotoxic drugs, oligonucleotides, toxins and radioactive molecules. The liposomes, peptides, and antibodies may also comprise compounds such as anti-VEGF aptamers described in (Ng et al 2006).

In some embodiments, the liposomes, peptides, or antibodies are provided in formulation with pharmaceutically acceptable carriers, excipients, and diluents, of which a wide variety are known in the art. These pharmaceutical carriers, excipients, and diluents include those listed in the USP pharmaceutical excipients listing. USP and NF Excipients, Listed by Categories, p. 2404-2406, USP 24 NF 19, United States Pharmacopeial Convention Inc., Rockville, Md. (ISBN 1-889788-03-1). Pharmaceutically acceptable excipients, such as vehicles, adjuvants, carriers, or diluents, are readily available to the public. Moreover, pharmaceutically acceptable auxiliary substances, such as pH adjusting and buffering agents, tonicity adjusting agents, stabilizers, wetting agents and the like, are readily available to the public.

Suitable carriers include, but are not limited to, water, dextrose, glycerol, saline, ethanol, and combinations thereof. The carrier can contain additional agents such as wetting or emulsifying agents, pH buffering agents, or adjuvants which enhance the effectiveness of the formulation. Topical carriers include liquid petroleum, isopropyl palmitate, polyethylene glycol, ethanol (95%), polyoxyethylene monolaurate (5%) in water, or sodium lauryl sulfate (5%) in water. Other materials such as anti-oxidants, humectants, viscosity stabilizers, and similar agents can be added as necessary. Percutaneous penetration enhancers such as Azone can also be included.

In pharmaceutical dosage forms, the compositions of the disclosure can be administered in the form of their pharmaceutically acceptable salts, or they can also be used alone or in appropriate association, as well as in combination, with other pharmaceutically active compounds. The subject compositions are formulated in accordance to the mode of potential administration.

The liposomes, peptides, and antibodies of the disclosure can be formulated into preparations for injection by dissolving, suspending or emulsifying them in an aqueous or non-aqueous solvent, such as vegetable or other similar oils, synthetic aliphatic acid glycerides, esters of higher aliphatic acids or propylene glycol, and if desired, with conventional additives such as solubilizers, isotonic agents, suspending agents, emulsifying agents, stabilizers, and preservatives. Other formulations for oral or parenteral delivery can also be used, as conventional in the art.

VII. METHODS OF TREATMENT

A. Routes of Administration, Dosage, and Frequency

Peptides or liposomes of the disclosure comprising therapeutic drugs may be administered to a subject in need of treatment by injection systemically, such as by intravenous injection, or by injection or application to the relevant site, such as by direct injection into a tumor, or direct application to the site when the site is exposed in surgery, or by topical application, such as if the disorder is on the skin, for example. A subject in need of treatment includes a subject suffering from a disease such as cancer, including HCC or liver cancer.

The peptides of the disclosure could be used to target antibodies to cancer for treatment. In one embodiment, a peptide of the disclosure is administered to a subject in need of treatment, followed by administration of an antibody that binds specifically to the peptide. The targeted antibodies may mediate antibody-dependent cell cytotoxicity or complement-dependent cytotoxicity, or may modify the underlying function of the target molecule. Such antibodies can be used in the form of antibody conjugates to directly deliver agents with a therapeutic effect on the target tissue. Such agents include radionuclides, toxins, chemotherapeutics, anti-VEGF aptamers and anti-angiogenic compounds.

Administration can be achieved in various ways, including oral, buccal, nasal, rectal, parenteral, intraperitoneal, intradermal, transdermal, subcutaneous, intravenous, intra-arterial, intracardiac, intraventricular, intracranial, intratracheal, and intrathecal administration, or otherwise by implantation or inhalation. Thus, the subject compositions can be formulated into preparations in solid, semi-solid, liquid, or gaseous forms, such as tablets, capsules, powders, granules, ointments, solutions, suppositories, injections, inhalants and aerosols. The following methods and excipients are merely exemplary and are in no way limiting.

Suitable excipient vehicles are, for example, water, saline, dextrose, glycerol, ethanol, or the like, and combinations thereof. In addition, if desired, the vehicle can contain minor amounts of auxiliary substances such as wetting or emulsifying agents or pH buffering agents. Actual methods of preparing such dosage forms are known, or will be apparent, to those skilled in the art. The composition or formulation to be administered will, in any event, contain a quantity of the agent adequate to achieve the desired state in the subject being treated.

Generally, compositions of the present are administered to a patient at a dose ranging from about 1 µg/kg to about 20 mg/kg, about 1 µg/kg to about 10 mg/kg, about 1 µg/kg to about 1 mg/kg, about 10 µg/kg to about 1 mg/kg, about 10 µg/kg to about 100 µg/kg, about 100 µg to about 1 mg/kg, or about 500 µg/kg to about 1 mg/kg. Antibodies are administered as a bolus dose, to maximize the interval of time that the antibodies can circulate in the patient's body following their administration to the patient. Continuous infusion may also be used after an initial bolus dose. Dosing can be in one dose, or at intervals such as once daily, once weekly, or once monthly. Dosage schedules can be adjusted based on, for example, the affinity of the polypeptide for hepatocellular carcinoma cells, the half-life of the polypeptide, and the severity of the patient's condition.

B. Combination Therapy

Peptides or liposomes of the disclosure can be used as monotherapy. Alternatively, the peptides or liposomes of the disclosure can be used in combination with standard chemotherapeutic or radiation regimens to treat cancers.

Drugs employed in cancer therapy may have a cytotoxic or cytostatic effect on cancer cells, or may reduce proliferation of the malignant cells. A liposome, peptide or antibody of the disclosure can be combined with radiation therapy. A liposome, peptide, or antibody of the disclosure may be used adjunctively with therapeutic approaches described in De Vita, et al., eds. (2001). For those combinations in which a liposome, peptide, or antibody of the disclosure and a second anti-cancer agent exert a synergistic effect against cancer cells, the dosage of the second agent may be reduced, compared to the standard dosage of the second agent when administered alone. A method for increasing the sensitivity of cancer cells comprises co-administering a liposome, peptide, or antibody of the disclosure with an amount of a chemotherapeutic anti-cancer drug that is effective in enhancing sensitivity of cancer cells. Co-administration may be simultaneous or non-simultaneous administration. A liposome, peptide, or antibody of the disclosure may be administered along with other therapeutic agents, during the course of a treatment regimen. In one embodiment, administration of a liposome, peptide, or antibody of the disclosure and other therapeutic agents is sequential. An appropriate time course may be chosen by the physician, according to such factors as the nature of a patient's illness, and the patient's condition.

VIII. DIAGNOSTIC METHODS

Detection of disease-specific biomarkers provides an effective screening strategy. Early detection provides not only early diagnosis, but in the case of cancer, can provide the ability to screen for polymorphisms and detect post-operative residual tumor cells and occult metastases, an early indicator of tumor recurrence. Early detection of disease-specific biomarkers can thus improve survival in patients before diagnosis, while undergoing treatment, and while in remission.

The peptides of the disclosure can be used as a diagnostic or prognostic for diseases, including cancer. The peptides can be used as diagnostics in a number of ways, including but not limited to ELISA, Western blot, fluorescence, immunofluorescence, immunohistochemistry, or autoradiography.

The antibodies of the present disclosure can also be used in combination with the peptides of the disclosure to detect liver cancer. In some embodiments, the assay is a binding assay that detects binding of an antibody with a peptide of the disclosure that has bound to a liver cell cancer cell, such as an hepatocellular carcinoma cell. The subject polypeptide or antibody can be immobilized, while the subject polypeptide and/or antibody can be detectably labeled. For example, the antibody can be directly labeled or detected with a labeled secondary antibody. That is, suitable, detectable labels for antibodies include direct labels, which label the antibody to the protein of interest, and indirect labels, which label an antibody that recognizes the antibody to the protein of interest. In another embodiment, the peptide comprises a label, and the binding of the peptide to a tissue is detected by assaying for the presence of the label.

IX. SCREENING METHODS

The disclosure provides a methods for identifying biological molecules that bind to peptides of the disclosure. Such molecules may be cell-surface molecules that may serve as targets for therapies or diagnostics that bind to the molecule. For example, a peptide specific for the molecule or antibodies that bind the molecule may be used to treat or diagnose a patient whose cells produce the molecule.

In one method, the peptides of the disclosure can be used as "bait proteins" in a two-hybrid assay or three-hybrid assay (see, e.g., U.S. Pat. No. 5,283,317; Zervos et al. (1993);

Madura et al. (1993); Bartel et al. (1993); Iwabuchi et al. (1993); and Suter et al. (2006) to identify other proteins, which bind to or interact with peptides of the disclosure.

In another method, peptides of the disclosure are incubated with cellular extracts to identify biological molecules that bind to peptides of the disclosure. In one method, the peptides of the disclosure are immobilized on a solid support, such as an HPLC column, and cellular extracts are exposed to immobilized peptides under conditions facilitating the binding of the peptides of the disclosure to target molecules. Bound molecules are eluted and identified through standard techniques such as mass-spectrometry.

EXAMPLES

The specification is most thoroughly understood in light of the teachings of the references cited within the specification. The following embodiments within the specification provide an illustration of embodiments of the disclosure and should not be construed to limit the scope of the disclosure. The skilled artisan readily recognizes that many other embodiments are encompassed by the disclosure.

I. Example 1

Phage-Displayed Random Peptide Libraries and Biopanning

A. Cell Lines and Cell Culture

59T, Changliver, HA22T, Hep3B, HepG2, J5, NTUBL, Mahlavu and SKHepl, all human hepatocellular carcinoma lines, and NNM, human primary normal nasomucosal epithelia (8), were used. HCC cells were obtained courtesy of Dr. Hsiao M. (Genomic Research Center, Academia Sinica, Taiwan). All the human HCC cell lines and NNM were maintained in Dulbecco's modified Eagle's medium (DMEM) and 10% fetal bovine serum (FBS) at 37° C. in a humidified atmosphere of 5% or 10% $CO_2$ in air.

Additional useful cell lines include, human lung squamous cell carcinoma line A549, high metastatic human lung adenocarcinoma line CL1-5, human lung adenocarcinoma line H23, human lung large cell carcinoma line H460, human lung cancer line PC13, human nasopharyngeal carcinoma line NPC-TW01, human oral squamous cell carcinoma line SAS, human pancreas carcinoma PaCa, colon (HCT116), breast (BT483), prostate (PC3), NNM, human normal nasal mucosal epithelia, and fibroblast. A549, H23, H460, PC13, PaCa, HCT116, PC3, Mahlavu and SAS are available from the American Type Culture Collection. CL1-5 and NPC-TW01 cell lines were established by (Chu et al., 1997) and (Lin et al., 1990), respectively.

B. Isolation of Phages Binding to HCC Cells

A phage-displayed random peptide library was used to select HCC, Mahlavu, cell-specific phages. Phage-displayed random peptide libraries (RPLs) Ph.D.-12 kit (New England Biolabs, Ipswich, Mass., USA) was employed in our experiments. Biopanning procedures were carried out according to a previous study (35) with some modifications. Briefly, Mahlavu cells were grown to 70-80% confluence, washed with phosphate buffer saline (PBS), harvested with 5 mM EDTA in PBS, and collected with serum free medium containing 1% BSA. Cell suspension was chilled at 4° C. before adding $1.5 \times 10^{11}$ plaque forming unit (pfu) of phage-displayed peptide library. The reaction mixture was incubated at 4° C. for 1 h, transferred to the top of a nonmiscible organic solvent (dibutyl phthalate:cyclohexane 9:1) (Sigma-Aldrich, Saint Louis, Mo., USA), and centrifuged. The phage-bound cell pellet was resuspended with LB medium and the phages were amplified and titrated with *Escherichia coli* ER2738 culture (New England Biolabs, Ipswich, Mass., USA). Recovered phages were subjected to additional rounds of biopanning with Mahlavu cells. The fifth round phage elute was titrated on LB/IPTG/X-Gal plates for phage clone identification. After five rounds of affinity selection (biopanning), the recovery rate of the fifth round had increased 3.5-fold over that observed in the first round (FIG. 1).

C. Identification of Phage Clones by ELISA

Ninety-six phage clones were randomly isolated and used to react with HCC cells and normal epithelial cells (NNM) by ELISA assay. About $1 \times 10^4$ Mahlavu and NNM cells were seeded separately in the 96 well ELISA plates and allowed to grow overnight. The plates were washed with serum free DMEM and blocked with serum free DMEM medium containing 1% BSA at 4° C. Then $10^9$ pfu of individual phage clones were added and incubated at 4° C. for 1 h. The plates were washed with PBS, and horseradish peroxidase (HRP)-conjugated anti-M13 antibody (Amersham Biosciences, Piscataway, N.J., USA) was added and incubated at 4° C. for 1 h. The plates were washed with PBS followed by incubation with the peroxidase substrate o-phenylenediamine dihydrochloride (OPD; Sigma-Aldrich, Saint Louis, Mo., USA). The reaction was terminated by 3NHC1, and optical density was determined using a microplate reader at 490 nm.

II. Example 2

Flow Cytometry and Biopsy Analyses

A. Identification of Phage Clones Specifically Binding to HCC Cells

To analyze the phage clones specifically binding to HCC cells, flow cytometry analysis was performed. HCC cells were grown to 70-80% confluence and harvested with 5 mM EDTA in PBS. HCC cells were resuspended in FACS buffer (PBS with 1% FBS) and incubated at 4° C. for 1 h with PC94 or control phage, which does not encode a protein, respectively. After washing with FACS buffer, HCC cells were incubated with monoclonal anti-M13 antibody at 4° C. for 1 h followed by 30 min incubation with anti-mouse antibody conjugated to R-phycoerythrin (Southern Biotech, Birmingham, Ala., USA). Analysis was performed on FACS-Calibur using CellQuest software (BD Bioscience, San Jose, Calif., USA).

Figure 2A:
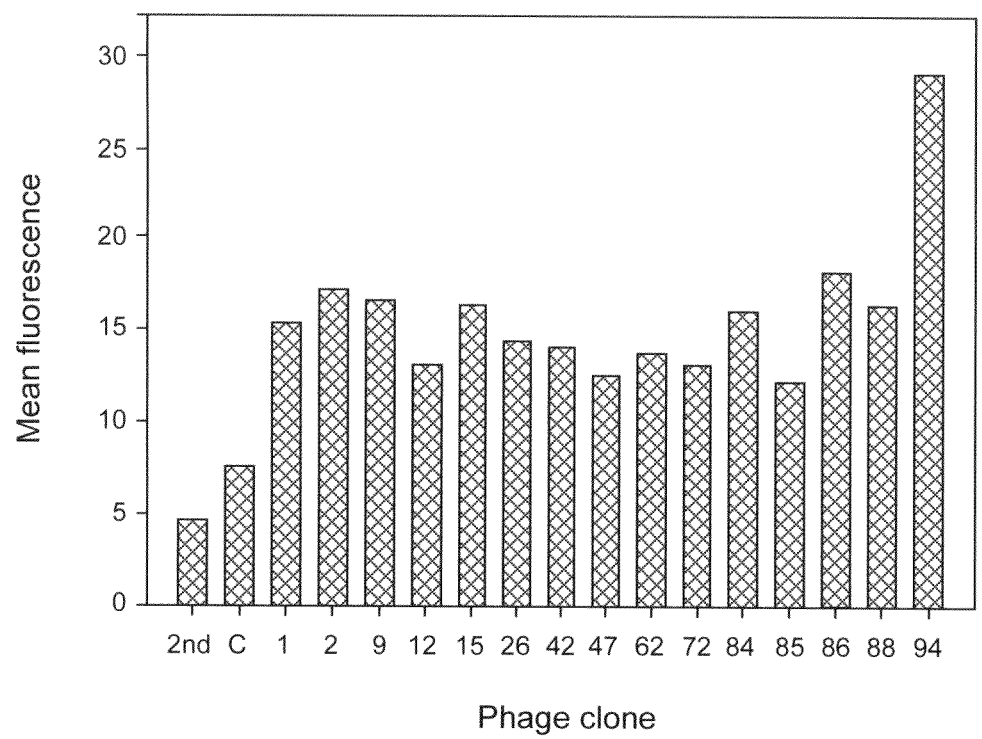

The results revealed that phage clone 94 (PC94) had the best reactivity to HCC cells while the rest of the phage clones showed moderate binding activity to HCC cells (FIG. 2A). (A) The surface binding activity of each selected phage to HCC cells was determined by flow cytometry (2nd: cells were stained with R-phycoerythrin conjugated anti-mouse-IgG; C: cells were incubated with control phage).

Figure 2B:
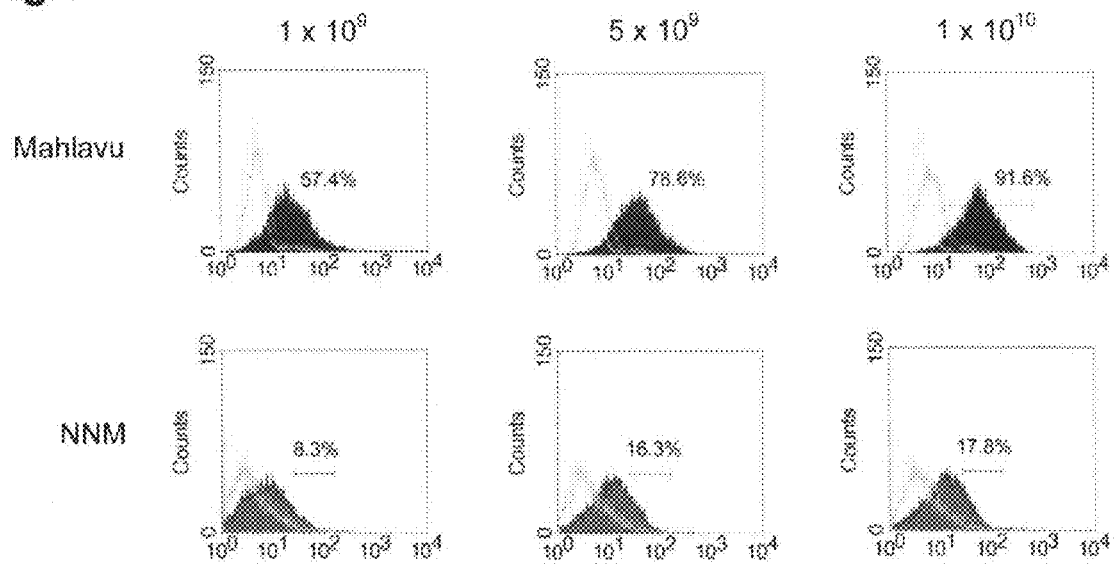

The binding activity of PC94 was further verified by incubating different dosages of phages with HCC cells, and analyzed by FACS. The results showed that the binding of PC94 to HCC cells occurs in a dose-dependent manner (FIG. 2B). In addition, no reactivity was found with the control helper phage, nor when PC94 was incubated with NNM (FIG. 2B). These results reveal that HCC, Mahlavu cells express an unknown molecule that can be recognized by the peptide displayed on PC94.

Figure 2C:
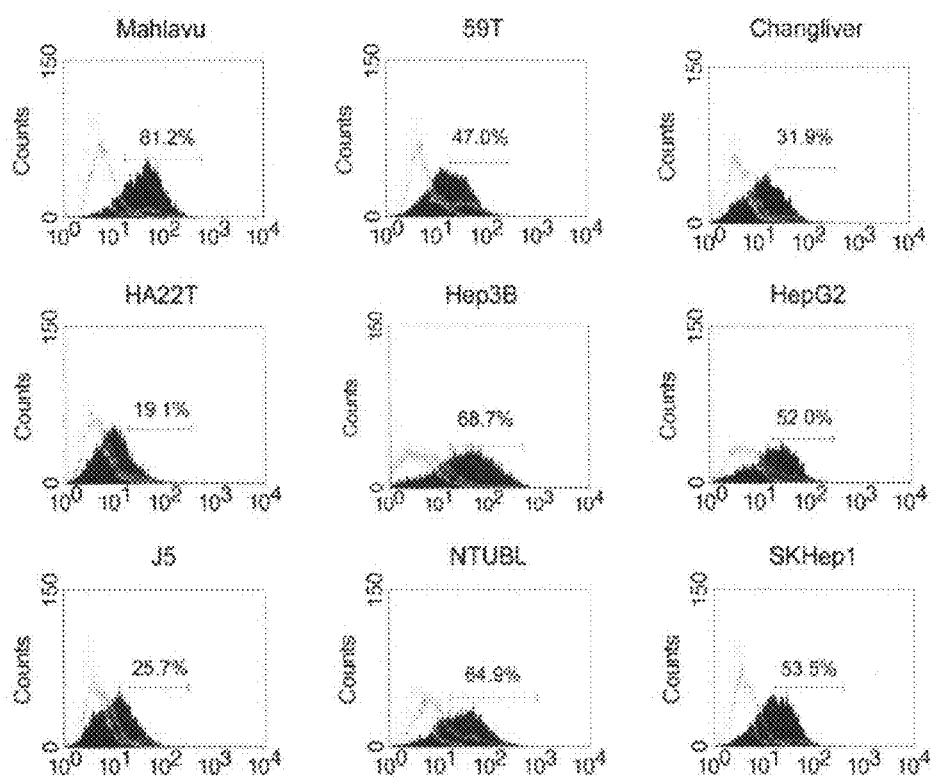

To investigate whether other HCC cells can be recognized by PC94, nine HCC cell lines were incubated with PC94 and analyzed by FACS. The results show that 6 of 9 HCC cell lines (Mahlavu, 59T, Hep3B, HepG2, NTUBL and SKHepl) react strongly (47~81.2%) with PC94 while other HCC cell lines (Changliver and J5) have moderate reactivity (25.7~31.9%), and the HA22T cell line is only weakly reactive (19.1%) (FIG. 2C). The surface binding activity of PC94 to each HCC cell line was analyzed (yellow: staining with R-phycoerythrin conjugated anti-mouse-IgG; orange: cells incubated with control phage). The results show that all of these cell lines express a target molecule that can be recognized by the PC94-displayed peptide (FIG. 2C).

Figure 2D:
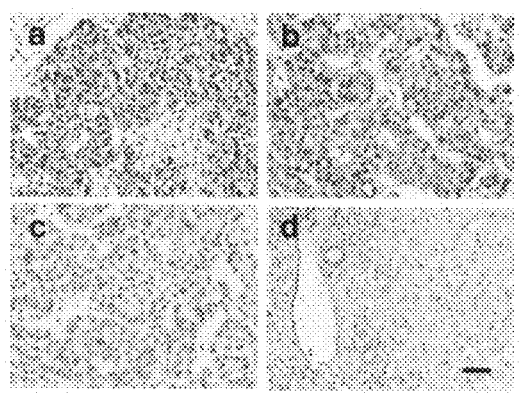

The binding specificity of PC94 for HCC cells was further tested using surgical specimens from HCC patients by immunohistochemistry. The results show that PC94 can recognize the tumor cells in surgical specimens of HCC (FIG. 2D, a and b) but not their normal counterparts (FIG. 2D, d). The control phage reveals no immuno-reactivity in the tumor tissues of the HCC surgical specimens (FIG. 2D, c). Biopsy specimens from HCC patients incubated with PC94 or control phage were detected using HRP-conjugated anti-M13 phage antibody. PC94 immuno-reactivity was found in the tumor tissues (D, a and b) but not in their normal counterparts (D, d). Control phage could not bind to these biopsy specimens (B, c) (Bar, 50 μm).

For localization of the peptide binding ability on liver cancer tissue, paraffin sections of human hepatocellular carcinoma were incubated with phage-displayed and biotin-labeled peptides using routine immunohistochemical procedures. The surgical specimens were obtained from the tissue bank of National Taiwan University Hospital (NTUH) with approval from the Institutional Review Board in NTUH (IRB9461702021).

B. DNA Sequencing and Computer Analysis

Fifteen phage clones (PC 1, 2, 9, 12, 15, 26, 42, 47, 62, 72, 84, 85, 86, 88 and 94) with higher HCC cell reactivity by ELISA and flow cytometry (FIG. 2A) were selected and sequenced. The phage DNA was extracted according to the manufacturer's instructions. The DNA sequences of purified phages were determined by di-deoxynucleotide chain termination method using an automated DNA sequencer (ABI PRISM 377; Perkin-Elmer, Waltham, Mass., USA). The sequencing was performed with the −96 gIII sequencing primer 5'-CCCTCATAGTTAGCGTAACG-3'(SEQ ID NO: 31). The phage-displayed peptide sequences were translated and aligned using a Genetic Computer Group (GCG) program. The phage-displayed peptide sequences were aligned by GCG software and revealed distinct consensus motif sequences (Table 1). The corresponding DNA sequences appear in Table 2.

Based on the GCG alignment (Table 1), PC94 and PC88 both displaying the motif, Pro-Ile/Leu-Leu-Pro (P-I/L-L-P) (SEQ ID NO: 33), were selected. The sequence identification numbers associated with the component sequences are SEQ ID NO: 34 (Pro-Ile-Leu-Pro) and SEQ ID NO: 35 (Pro-Leu-Leu-Pro).

III. Example 3

Animal Model for In Vivo Targeting Assay and Peptide Competition Assay

Several issues were addressed to evaluate the potential of SP94, the polypeptide encoded by PC94, as a drug delivery director for targeted drug delivery against HCC. First, we investigated whether SP94 could be targeted to HCC cells in vivo. We examined the tumor homing ability of PC94 and its competitive inhibition by SP94 in a HCC xenograft model. In vivo homing experiments showed that PC94 has homing ability to tumor tissues, with a binding activity over 8-fold higher than that of the control phage (FIG. 3A). Moreover, in peptide competitive inhibition experiments, SP94 inhibited PC94 binding to the tumor mass, while the same concentration of a control peptide had no such inhibitory effect (FIG. 3B).

A. Animal Model for PC94 Targeting

To verify the targeting ability of PC94 in vivo, mice bearing Mahlavu-derived HCC xenografts (500 mm$^3$) were injected with PC94 or control phage through the tail vein. Phages circulated and were then perfused. Phage particles that bound to the tumor tissue and normal visceral organs were recovered. The results demonstrated that significantly more PC94 phage particles were recovered (normalized per gram of tissue) from tumor tissue than from normal organs, such as brain (220-fold), heart (32-fold) and lungs (23-fold). However, the control phage revealed no homing phenomenon, neither in tumor tissue nor in normal organs (FIG. 3A).

SCID mice (4-6 weeks old) were injected subcutaneously (s.c.) into the dorsal-lateral flank with 5×10$^6$ Mahlavu cells. Mice bearing Mahlavu-derived xenografts (500 mm$^3$) were injected intravenously (i.v.) with 2×10$^9$ pfu of PC94 or control phage. After perfusion, the organs (brain, heart, and lungs) and tumor tissue were removed, washed with cold PBS and weighed. The phage bound to the tumor tissue and organs were rescued by *Escherichia coli* ER2738 culture. The eluted phage particles were titrated on LB/IPTG/X-Gal plates. In peptide competitive inhibition experiments, 2×10$^9$ pfu of PC94 phage was co-injected with 100 μg of SP94 peptide or the control peptide. The tissue distribution of targeting phages in the tumor-bearing mice was examined by immunohistochemical staining. The tissue sections were incubated with mouse anti-M13 antibody, followed by incubation with biotinylated horse anti-mouse antibody (ABC kit; Vector Laboratories, Burlingame, Calif., USA) and washed with PBS, then immersed with ABC reagent. The sections were immersed in DAB solution plus 0.01% hydrogen peroxide, washed with PBS and mounted with 50% glycerol in PBS.

B. Peptide Competition Assay

Peptide competitive inhibition assay (FIG. 3) confirmed that the binding activity of PC94 to HCC cells was dependent on the PC94-displayed peptide rather than another part of the phage particles. These results strongly indicate that the plasma membranes of these HCC cells express an unknown target molecule, such as a protein, which can be recognized by both the synthetic peptide SP94 and the PC94-displayed peptide, but not by other parts of the phage.

1. Peptide Synthesis and Labeling

Targeting SP94 (SFSIIHTPILPL) (SEQ ID NO: 2) and control (FPWFPLPSPYGN) (SEQ ID NO: 32) peptides were synthesized and purified by reverse-phase high-performance liquid chromatography to >95% purity by the peptide synthesis core facility, Institute of Biological Chemistry, Academia Sinica. Biotin-labeled peptides (Biotin-SP94 and biotin-control-peptide) were synthesized by conjugating a biotin molecule to the peptide amino terminus. Mass spectrometry confirmed the predicted mass.

Mice bearing HCC xenografts were co-injected with PC94 and the cognate synthetic peptide SP94. The results showed that SP94 markedly inhibited recovery of phage particles from tumor tissue. One hundred micrograms of SP94 inhibited 88% of PC94 binding to tumor tissue, but the same concentration of a control peptide (con-P) had no such inhibitory effect (FIG. 3B).

For verification of the tissue distribution of PC94, tissue sections of tumor and normal organs derived from the homing and competition experiments were immunostained by anti-phage antibody. It was found that only tumor cells revealed immuno-reactivity (FIG. 3C, d and e), but not normal organs such as brain (FIG. 3C, a), heart (FIG. 3C, b) and lungs (FIG.

3C, c). However, when PC94 was co-injected with the cognate synthetic peptide SP94, no immuno-reactivity was found in the tumor tissue (FIG. 3C, j). Neither tumor cells nor normal organs were found to have immuno-reactivity with control phage (C, f to i) (Bar, 50 µm).

To examine whether SP94 could increase the therapeutic index of targeted drugs, we investigated the binding specificity of SP94 to tumor tissues but not normal organs. In both the homing ability assay and the peptide competitive inhibition experiments, PC94 was found to bind specifically to tumor tissues but not to normal visceral organs, such as brain, heart, and lungs (FIGS. 3A and B). Immunohistochemical staining demonstrated that the PC94 particles were only localized in tumor tissues, but not in brain, heart, and lung tissues (FIG. 3C). Finally, we examined whether the SP94 peptide could recognize the target molecule produced by the tumor tissues of HCC patients. Both PC94 (FIG. 2D) and biotin-labeled SP94 recognized a target protein expressed on surgical specimens from HCC patients with a positive rate of 61.3% (19/31). Taken together, we conclude that SP94 specifically recognizes an unknown target molecule produced by HCC cells, but not by normal tissues. This molecule is therefore useful for targeted drug delivery against HCC, and SP94 provides a reagent for identifying this molecule.

IV. Example 4

In Vivo Tumor Targeted Therapeutic Studies

Figure 4A:
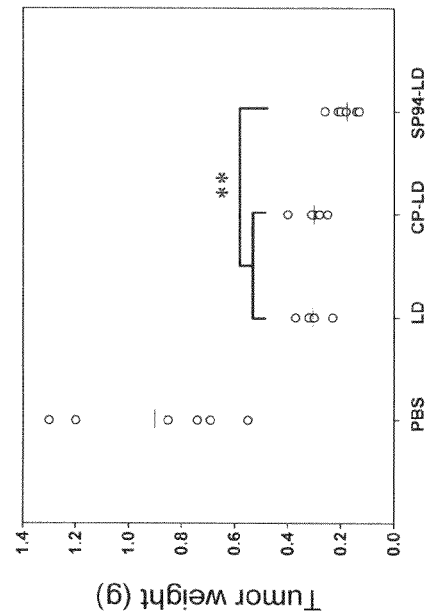
Figure 4B:
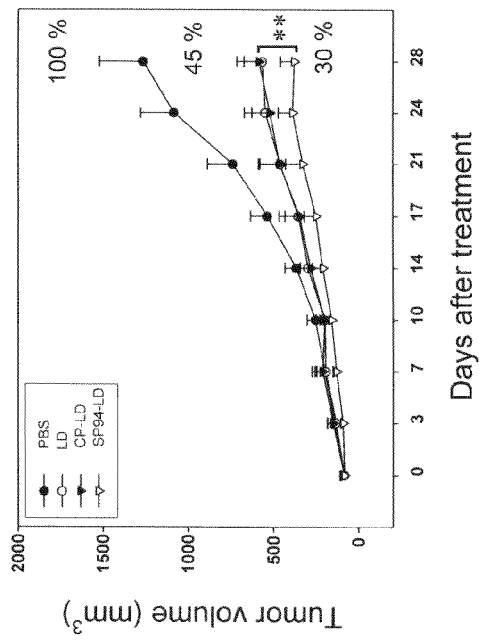
Figure 4C:
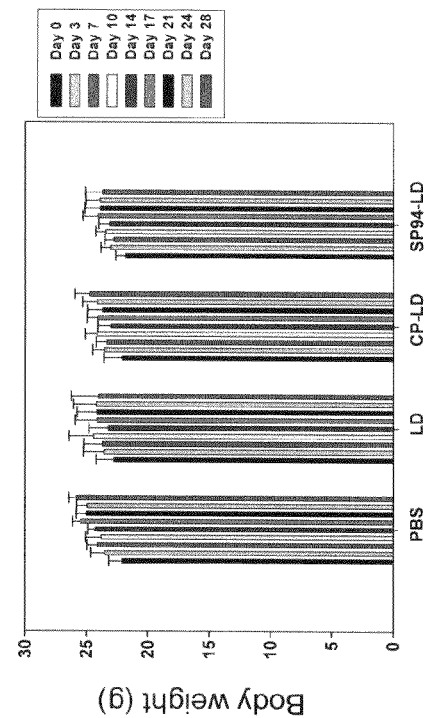
Figure 4D:
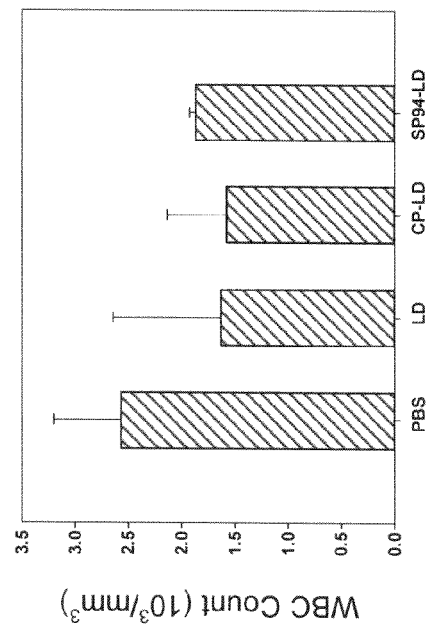
Figure 5A:
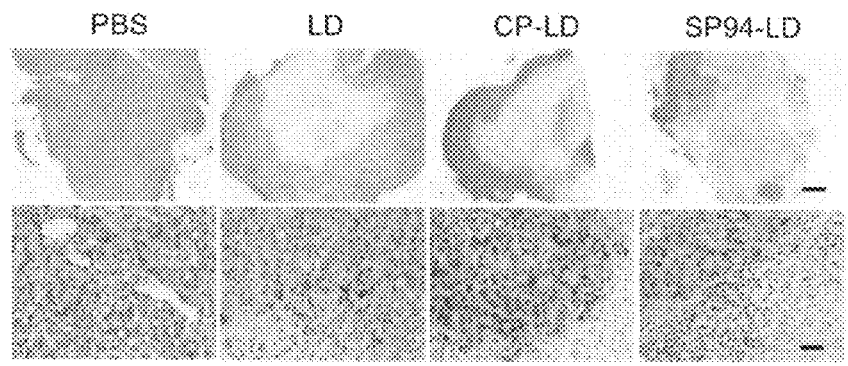
Figure 5B:
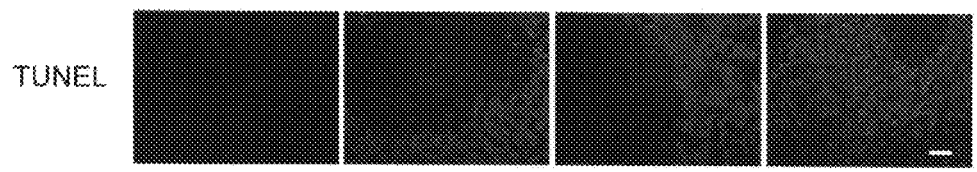
Figure 5C:
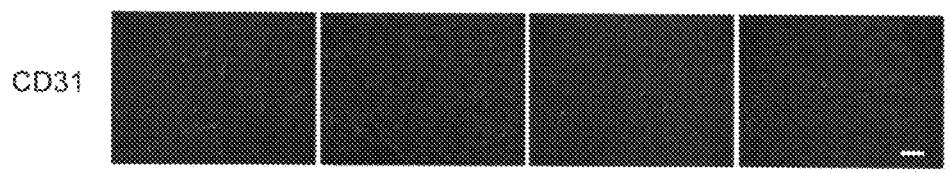
Figure 6A:
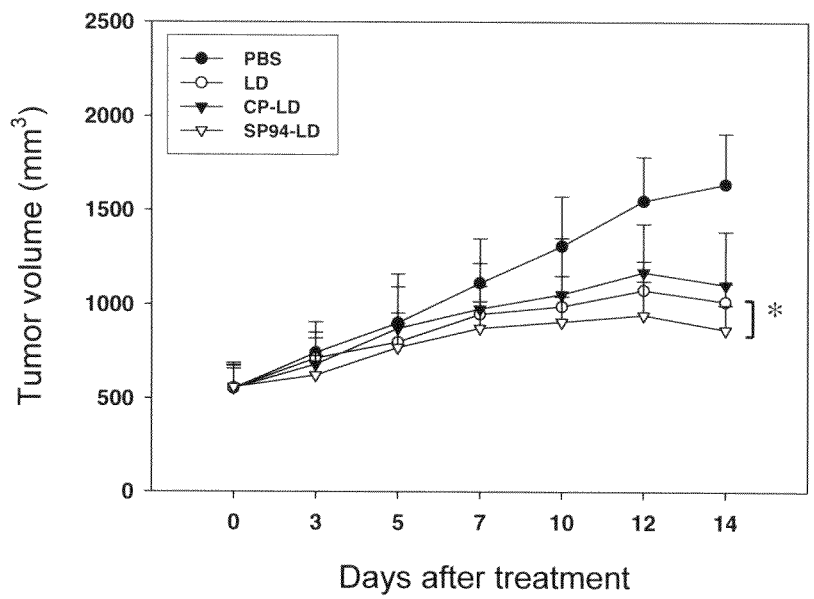
Figure 6B:
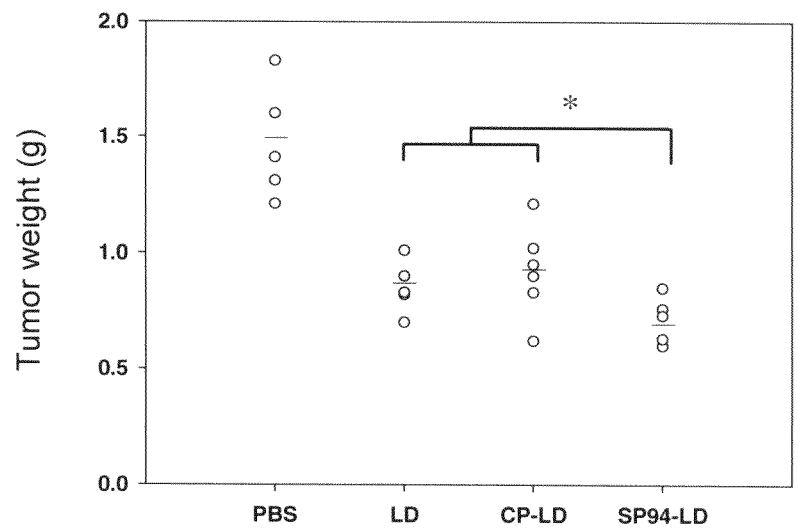
Figure 6C:
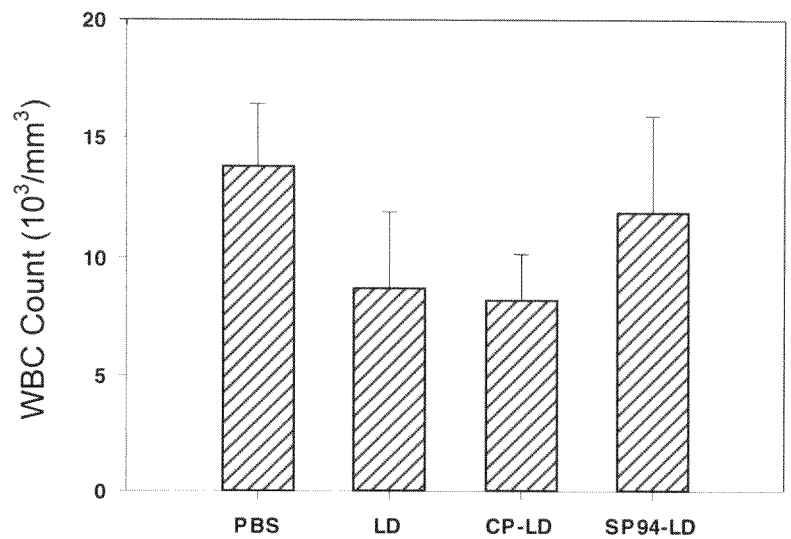
Figure 6D:
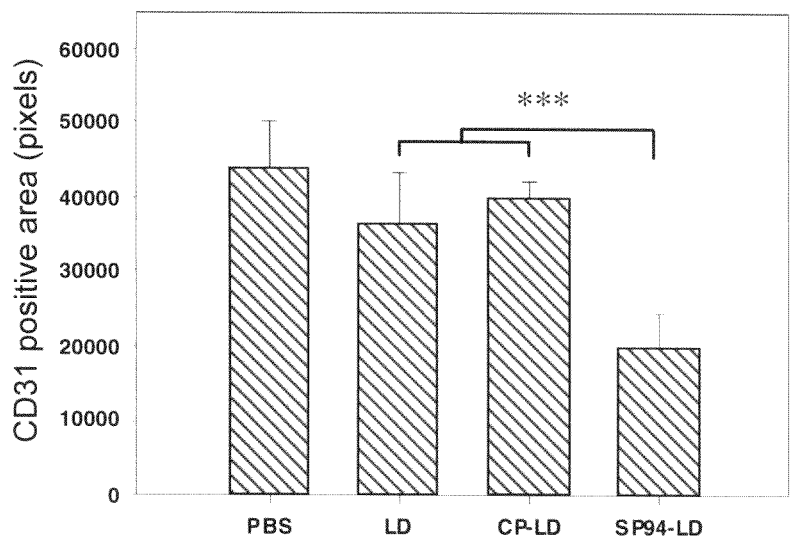

Using a combination of SP94 and PEGylated liposomal doxorubicin, a process called active or ligand-mediated targeting, the site-specific actions of this targeted DDS further enhanced the anti-tumor effects (FIGS. 4 and 6) and was accompanied by increased tumor apoptosis (FIGS. 5A, 5B and 6E) and decreased tumor angiogenesis (FIGS. 5C and 6D).

In clinical trials of formulations of PEGylated liposomal doxorubicin (Lipo-Dox), improved pharmacokinetic properties and reduced systemic toxicity have been observed (40). Here, our results revealed that with the site-specific actions of this targeted drug delivery system, SP94-Lipo-Dox, can further decrease hematological toxicities by avoiding the reduction in the total white blood cell count (WBC) (FIGS. 4C and 6C). Reduction in the total WBC count observed with non-targeted PEGylated liposomal doxorubicin (Con-P-Lipo-Dox and Lipo-Dox) may be due to its increased circulation time, confinement in blood vessels and the increased chances of its non-specific uptake by mononuclear phagocytic system cells. Such leukopenia has already been reported in a phase II clinical trial of PEGylated liposomal doxorubicin for patients with advanced HCC (41, 42).

Some previous studies of the phase II clinical trial of PEGylated liposomal doxorubicin have reported that the drug exhibited almost no activity in advanced HCC, with response rates of 0-14% at best (41-43). The enhanced therapeutic efficacy of SP94-Lipo-Dox described here therefore indicates significant clinical potential for this targeted drug delivery system in the treatment of advanced HCC patients. In addition, identification of the target molecule interacting with SP94 would enable verification of its specific expression on HCC tumor tissue and authenticate its use as a target for HCC therapy.

The targeted drug delivery system comprises: an anti-cancer drug, a targeting ligand, and may further comprise a carrier. Since doxorubicin has been reported to provide the most consistent overall response rate (18%) in HCC (36) and liposomal doxorubicin has also been shown to have remarkable activities in refractory breast and ovarian cancers (37, 38), this drug was chosen as the anti-cancer agent and polyethylene glycol coated liposome (PEGylated liposome) was chosen as the carrier. PEGylated liposomal doxorubicin was coupled with SP94 (SP94-Lipo-Dox) to assess the efficacy of targeted drug delivery against HCC. In the human HCC xenograft model, SP94-Lipo-Dox showed an improvement in therapeutic efficacy compared with control peptide conjugated Lipo-Dox (Con-P-Lipo-Dox) and Lipo-Dox treated groups (FIGS. 4 and 6).

Without being bound by any particular mechanism, the partial inhibition of tumor growth of Con-P-Lipo-Dox and Lipo-Dox treated groups may be accounted for by the following factors. First, the leakiness of the angiogenic tumor vasculature may allow selective extravasation of drug conjugates in tumor tissue. In addition, drug conjugates may be retained in tumor tissue due to the lack of an effective lymphatic drainage. These factors may result in passive targeting and accumulation of the drug conjugates in tumor tissue (14). It has also been shown in animal studies that long-circulating PEGylated liposomal doxorubicin leads to passive preferential localization in tumors, and results in a several-fold increase of drug concentration in the tumor relative to that obtained with free drugs (15, 39).

A. Preparation and Administration of Peptide-Liposomal Doxorubicin

Procedures for preparation of peptide-liposomal doxorubicin have been described (8). Briefly, peptides were coupled to NHS-PEG-DSPE [N-hydroxysuccinimido-carboxyl-PEG (Mw, 3400) derived distearoylphosphatidyl ethanolamine (NOF Corporation, Tokyo, Japan)] in a 1:1.5 molar ratio. The coupling reaction was done with the free amine group in the amino terminus of the peptide to produce peptidyl-PEG-DSPE and confirmed by quantitation of the remaining amino groups with trinitrobenzenesulfonate reagent (Sigma-Aldrich, Saint Louis, Mo., USA). Peptidyl-PEG-DSPE was transferred to pre-formed PEGylated liposomal doxorubicin after co-incubation at temperature above the transition temperature of the lipid bilayer.

SCID mice (4-6 weeks old) were injected s.c. into the dorsal-lateral flank with $5 \times 10^6$ Mahlavu cells. Tumor-bearing mice (100 $mm^3$) were then randomly assigned into four groups (six mice per group) for different treatments A: SP94-Lipo-Dox (SP94-LD); B: Con-P-Lipo-Dox (CP-LD); C: Lipo-Dox (LD) and D: PBS. Treatments were administered through tail vein injection, 1 mg/kg twice a week, for four consecutive weeks, with a total dose of 8 mg/kg. In another experiment, mice bearing larger Mahlavu-derived xenografts (550 $mm^3$) were assigned into four groups as described. Treatments were administered through tail vein injection, 5 mg/kg once a week, for two consecutive weeks, with a total dose of 10 mg/kg. Body weights and the tumor sizes were measured by electronic scales and calipers. The tumor volumes were calculated using the equation: length×(width)2× 0.52. At the end of the experiment, tumor tissue and the visceral organs of each mouse were removed and fixed with 3% formaldehyde and OCT embedded for further histopathological examination. Animal care was carried out in accordance with guidelines of Academia Sinica, Taiwan.

At the end of the treatment (Day 28), the tumor size of the Con-P-Lipo-Dox and Lipo-Dox group was 1.5-fold larger than that of the SP94-Lipo-Dox group. The tumor size of the control PBS group was 3.3-fold larger than that of the SP94-Lipo-Dox group. (P<0.01) (FIG. 4A). In addition, the group of tumor bearing mice that received SP94-Lipo-Dox was found to have a lower tumor weight, about 40% inhibition compared with that in the Con-P-Lipo-Dox and Lipo-Dox treated groups (P<0.01) (FIG. 4B). Error bars in the graphs represent standard errors, and P values were calculated by Student's t test.

1. Total WBC Count

Blood was extracted from the submaxillary vein and mixed gently with 15% EDTA solution to prevent coagulation. RBC lysis buffer containing 2% acetic acid and 1% of Gentian violet (Sigma-Aldrich, Saint Louis, Mo., USA) was then added and incubated at room temperature. The total WBC was calculated using a hemacytometer.

In order to evaluate the side-effects caused by the systemic delivery of chemotherapeutic drugs, the total WBC count was determined. The results revealed that the total WBC count of the SP94-Lipo-Dox treated group ($1.9\times10^3/mm^3$) was higher than those of the Con-P-Lipo-Dox ($1.6\times10^3/mm^3$) and Lipo-Dox ($1.6\times10^3/mm^3$) treated groups, but lower than that of the PBS group ($2.6\times10^3/mm^3$) (FIG. 4C). The body weight did not significantly change in each treated group (FIG. 4D). Error bars in the graphs represent standard errors, and P values were calculated by Student's t test.

V. Example 5

Histopathological Examination, Immunofluorescent Detection of Tumor Blood Vessels and Apoptotic Cells in Peptide-Liposomal Doxorubicin Therapy A. TUNEL Staining The frozen tumor tissue sections were incubated with Terminal deoxy-nucleotidyl-transferase mediated dUTP nick end labeling (TUNEL) reaction mixture (Roche Diagnostic, Grenzacherstrasse, Basel, CHE) at 37° C. for 1 h. The slides were counterstained with Hoechst 33258 (Molecular Probes, Eugene, Oreg., USA) and mounted with mounting medium (Vector Laboratories, Burlingame, Calif., USA). Then the slides were visualized under a fluorescent microscope.

B. CD31 Staining

The frozen tumor tissue sections were fixed with methanol-acetone (1:1), washed with PBS and immersed in blocking buffer (1% BSA in PBS) followed by incubation with rat anti-mouse CD31 (BD Pharmingen, San Diego, Calif., USA). The sections were washed with $PBST_{0.1}$ (0.1% Tween-20 in PBS) and then incubated with rabbit anti-rat antibody (Stressgen, Ann Arbor, Mich., USA) and immersed in Rhodamine-labeled goat anti-rabbit antibody (Jackson ImmunoResearch, West Grove, Pa., USA). The slides were counterstained with Hoechst 33258, mounted with mounting medium and visualized under a fluorescent microscope.

The histopathology of tumor tissues in each treatment group was examined after staining with H&E. Marked disseminated necrotic/apoptotic areas were present in the whole section of SP94-Lipo-Dox treated xenografts, while moderate necrotic/apoptotic areas were found in the Lipo-Dox and Con-P-Lipo-Dox treated xenografts. The PBS treated group showed normal HCC cells (FIG. 5A). The whole section of the SP94-Lipo-Dox (SP94-LD) treated xenograft shows marked disseminated necrotic/apoptotic areas, while the Con-P-Lipo-Dox (CP-LD) and Lipo-Dox (LD) xenografts reveal moderate necrotic/apoptotic areas, and the PBS group shows normal HCC cells (Bars: upper panels, 500 μm and lower panels, 50 μm).

The sections were TUNEL labeled to visualize apoptotic tumor cells (green). The TUNEL-positive tumor cells were distributed more evenly in the SP94-Lipo-Dox treated group compared with the Con-P-Lipo-Dox and Lipo-Dox groups. No apoptotic tumor cells were found in the PBS treated group (Bar, 100 μm). (FIG. 5 B). TUNEL was used to identify apoptotic tumor cells and anti-CD31 antibodies were applied to detect tumor blood vessels. Representative microscopic fields from the tumors show more apoptotic tumor cells (FIG. 5B) and a lower density of blood vessels (FIG. 5C) in the SP94-Lipo-Dox treated group than in Con-P-Lipo-Dox and Lipo-Dox treated groups.

Figure 5D:
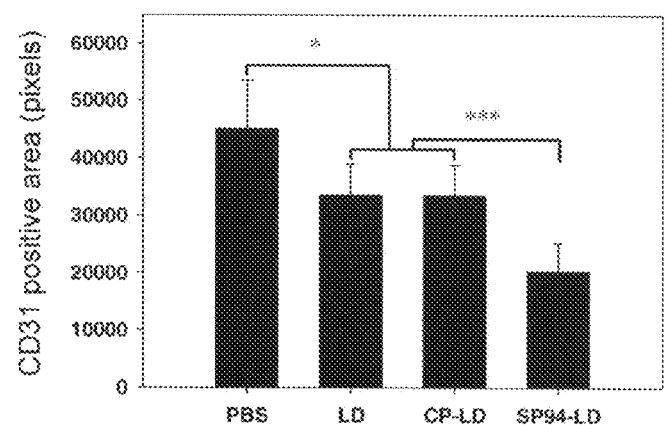

The sections were stained with anti-CD31 antibodies to visualize tumor blood vessels (red) and counterstained with H33258 (blue) (Bar, 100 μm). (FIG. 5C). Areas of CD31-positive endothelial cells were quantified (n=6) at low power magnification areas of CD31-positive endothelial cells were also quantified (n=6) under low power magnification. The areas of CD31-positive endothelial cells were markedly decreased in the Lipo-Dox and Con-P-Lipo-Dox treated groups compared with those in the PBS group (n=6, P<0.05). Areas of CD31-positive endothelial cells were more reduced in the SP94-Lipo-Dox treated group compared with those in Con-P-Lipo-Dox and Lipo-Dox groups (n=6, P<0.001) (FIG. 5D). High tumor vascular density and no apoptotic cells were found in the PBS treated group (FIGS. 5B and C). Error bars in the graphs represent standard errors, and P values were calculated by Student's t test.

VI. Example 6

Peptide-Liposomal Doxorubicin Therapy for Treatment of Large HCC Xenograft Tumors To verify whether large xenografts could also respond to SP94-Lipo-Dox treatment, mice bearing large HCC xenografts (550 mm³) were assigned into four groups for different treatments: A: SP94-Lipo-Dox (SP94-LD); B: Con-P-Lipo-Dox (CP-LD); C: Lipo-Dox (LD) and D: PBS. At the end of the treatment (Day 14), the tumor sizes of the Con-P-Lipo-Dox and Lipo-Dox group gradually increased to 1.3- and 1.2-fold larger than that of the SP94-Lipo-Dox (P=0.089, P<0.05 respectively). The tumor size of the control PBS group was 1.9-fold larger than that of the SP94-Lipo-Dox group (P<0.05) (FIG. 6A). In addition, the group of tumor bearing mice that received SP94-Lipo-Dox was found to have a lower tumor weight than the Con-P-Lipo-Dox, Lipo-Dox and PBS groups. Tumor weight of the Con-P-Lipo-Dox, Lipo-Dox and PBS groups increased to 1.3-, 1.2- and 2.1-fold larger than that of the SP94-Lipo-Dox group, respectively (P<0.05) (FIG. 6B). The total WBC count was also analyzed at day 10 and showed that the total WBC of the SP94-Lipo-Dox treated group ($11.8\times10^3/mm^3$) was higher than those of the Con-P-Lipo-Dox ($8.8\times10^3/mm^3$) and Lipo-Dox ($8.2\times10^3/mm^8$) treated groups, but lower than that of the PBS group ($13.9\times10^3/mm^3$) (FIG. 6C).

Figure 6E:
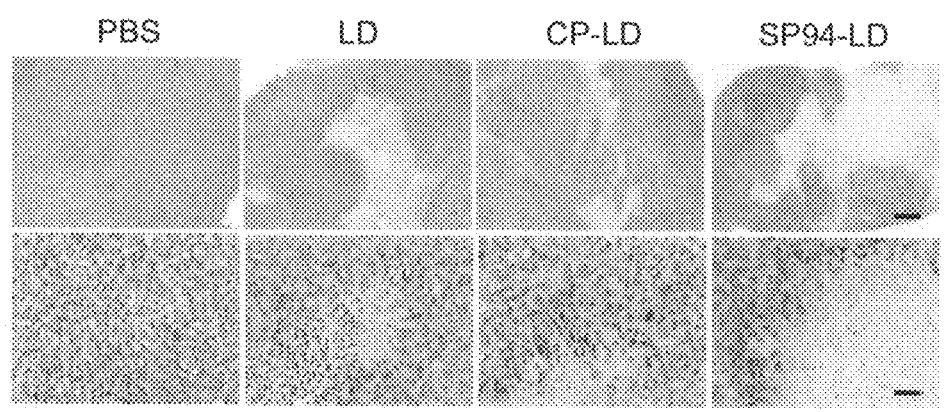

The histopathology of tumor tissue in each treatment group was examined by H&E staining. Marked necrotic/apoptotic areas were present in the whole sections from SP94-Lipo-Dox treated xenografts, while moderate necrotic/apoptotic areas were found in the Lipo-Dox and Con-P-Lipo-Dox treated xenografts, and the PBS group showed normal HCC cells (FIG. 6E). Areas of CD31-positive endothelial cells in the tumor tissues from each treatment were quantified (n=6) under low power magnification. The areas of CD31-positive endothelial cells were slightly decreased in the Lipo-Dox and Con-P-Lipo-Dox treated groups compared with those of the PBS group. However, areas of CD31-positive endothelial cells were significantly reduced in the SP94-Lipo-Dox treated group compared with those in Con-P-Lipo-Dox and Lipo-Dox groups (n=6, P<0.001) (FIG. 6D). (Bars: upper panels, 500 μm and lower panels, 50 μm). Error bars in the graphs represent standard errors, and P values were calculated by Student's t test.

The publications discussed herein are provided solely for their disclosure prior to the filing date of the present application. Nothing herein is to be construed as an admission that the present disclosure is not entitled to antedate such publication by virtue of prior invention. The citation of any publications herein is not an admission that such references are prior art to the present disclosure. Further, the dates of publication provided may be different from the actual publication dates which may need to be independently confirmed.

X. Example 7

Comparison of PC88 and PC94 in Binding

FACS analysis was conducted to compare the binding activity of PC88 and PC94. Mahlavu cells were incubated with $1 \times 10^9$, $5 \times 10^9$, $7.5 \times 10^9$ and $1 \times 10^{10}$ TU, respectively and the surface binding activity of individual phage clones was analyzed by FACS using the procedure described in Example 2. Mahlavu cell-binding activity of PC94 is better than PC88 (FIG. 7). Con-phage indicates the control phage.

XI. Example 8

Comparison of Tumor Homing of PC88 and PC94 In Vivo

The tumor homing ability of PC88 and PC94 was compared in SCID mice. SCID mice bearing HCC xenograft were injected i.v. with PC88, PC94 and control helper phage, and phages were recovered after perfusion as described in Example 3. The titer of phage recovered from the tumor, control organs such as brain, heart and lungs was determined on LB/IPTG/X-Gal plates. Tumor homing ability of PC94 is better than PC88 (FIG. 8).

VII. PUBLICATIONS

1. Thomas, M. B., and Zhu, A. X. (2005) Hepatocellular carcinoma: the need for progress. *J Clin Oncol* 23, 2892-2899.
2. Farazi, P. A., and DePinho, R. A. (2006) Hepatocellular carcinoma pathogenesis: from genes to environment. *Nat Rev Cancer* 6, 674-687.
3. Jemal, A., Murray, T., Ward, E., Samuels, A., Tiwari, R. C., Ghafoor, A., Feuer, E. J., and Thun, M. J. (2005) Cancer statistics, 2005. *CA Cancer J Clin* 55, 10-30.
4. Bosslet, K., Straub, R., Blumrich, M., Czech, J., Gerken, M., Sperker, B., Kroemer, H. K., Gesson, J. P., Koch, M., and Monneret, C. (1998) Elucidation of the mechanism enabling tumor selective prodrug monotherapy. *Cancer Res* 58, 1195-1201.
5. Allen, T. M., and Cullis, P. R. (2004) Drug delivery systems: entering the mainstream. *Science* 303, 1818-1822.
6. Allen, T. M., Mumbengegwi, D. R., and Charrois, G. J. (2005) Anti-CD19-targeted liposomal doxorubicin improves the therapeutic efficacy in murine B-cell lymphoma and ameliorates the toxicity of liposomes with varying drug release rates. *Clin Cancer Res* 11, 3567-3573.
7. MacDiamid, J. A., Mugridge, N. B., Weiss, J. C., Phillips, L., Burn, A. L., Paulin, R. P., Haasdyk, J. E., Dickson, K. A., Brahmbhatt, V. N., Pattison, S. T., James, A. C., Al Bakri, G., Straw, R. C., Stillman, B., Graham, R. M., and Brahmbhatt, H. (2007) Bacterially derived 400 nm particles for encapsulation and cancer cell targeting of chemotherapeutics. *Cancer Cell* 11, 431-445.
8. Lee, T. Y., Wu, H. C., Tseng, Y. L., and Lin, C. T. (2004) A novel peptide specifically binding to nasopharyngeal carcinoma for targeted drug delivery. *Cancer Res* 64, 8002-8008.
9. Xiong, X. B., Huang, Y., Lu, W. L., Zhang, X., Zhang, H., Nagai, T., and Zhang, Q. (2005) Enhanced intracellular delivery and improved antitumor efficacy of doxorubicin by sterically stabilized liposomes modified with a synthetic RGD mimetic. *J Control Release* 107, 262-275.
10. Vasey, P. A., Kaye, S. B., Morrison, R., Twelves, C., Wilson, P., Duncan, R., Thomson, A. H., Murray, L. S., Hilditch, T. E., Murray, T., Burtles, S., Fraier, D., Frigerio, E., and Cassidy, J. (1999) Phase I clinical and pharmacokinetic study of PK1 [N-(2-hydroxypropyl)methacrylamide copolymer doxorubicin]: first member of a new class of chemotherapeutic agents-drug-polymer conjugates. Cancer Research Campaign Phase I/II Committee. *Clin Cancer Res* 5, 83-94.
11. Duncan, R. (2003) The dawning era of polymer therapeutics. *Nat Rev Drug Discov* 2, 347-360.
12. Satchi-Fainaro, R., Mamluk, R., Wang, L., Short, S. M., Nagy, J. A., Feng, D., Dvorak, A. M., Dvorak, H. F., Puder, M., Mukhopadhyay, D., and Folkman, J. (2005) Inhibition of vessel permeability by TNP-470 and its polymer conjugate, caplostatin. *Cancer Cell* 7, 251-261.
13. Hashizume, H., Baluk, P., Morikawa, S., McLean, J. W., Thurston, G., Roberge, S., Jain, R. K., and McDonald, D. M. (2000) Openings between defective endothelial cells explain tumor vessel leakiness. *Am J Pathol* 156, 1363-1380.
14. Matsumura, Y., and Maeda, H. (1986) A new concept for macromolecular therapeutics in cancer chemotherapy: mechanism of tumoritropic accumulation of proteins and the antitumor agent smancs. *Cancer Res* 46, 6387-6392.
15. Northfelt, D. W., Martin, F. J., Working, P., Volberding, P. A., Russell, J., Newman, M., Amantea, M. A., and Kaplan, L. D. (1996) Doxorubicin encapsulated in liposomes containing surface-bound polyethylene glycol: pharmacokinetics, tumor localization, and safety in patients with AIDS-related Kaposi's sarcoma. *J Clin Pharmacol* 36, 55-63.
16. Papahadjopoulos, D., Allen, T. M., Gabizon, A., Mayhew, E., Matthay, K., Huang, S. K., Lee, K. D., Woodle, M. C., Lasic, D. D., Redemann, C., and et al. (1991) Sterically stabilized liposomes: improvements in pharmacokinetics and antitumor therapeutic efficacy. *Proc Natl Acad Sci USA* 88, 11460-11464.
17. Northfelt, D. W., Dezube, B. J., Thommes, J. A., Miller, B. J., Fischl, M. A., Friedman-Kien, A., Kaplan, L. D., Du Mond, C., Mamelok, R. D., and Henry, D. H. (1998) Pegylated-liposomal doxorubicin versus doxorubicin, bleomycin, and vincristine in the treatment of AIDS-related Kaposi's sarcoma: results of a randomized phase III clinical trial. *J Clin Oncol* 16, 2445-2451.
18. Stewart, S., Jablonowski, H., Goebel, F. D., Arasteh, K., Spittle, M., Rios, A., Aboulafia, D., Galleshaw, J., and Dezube, B. J. (1998) Randomized comparative trial of pegylated liposomal doxorubicin versus bleomycin and vincristine in the treatment of AIDS-related Kaposi's sarcoma. International Pegylated Liposomal Doxorubicin Study Group. *J Clin Oncol* 16, 683-691.
19. Harrington, K. J., Mohammadtaghi, S., Uster, P. S., Glass, D., Peters, A. M., Vile, R. G., and Stewart, J. S. (2001) Effective targeting of solid tumors in patients with locally advanced cancers by radiolabeled pegylated liposomes. *Clin Cancer Res* 7, 243-254.
20. Al-Batran, S. E., Bischoff, J., von Minckwitz, G., Atmaca, A., Kleeberg, U., Meuthen, I., Morack, G., Lerbs, W., Hecker, D., Sehouli, J., Knuth, A., and Jager, E. (2006) The clinical benefit of pegylated liposomal doxorubicin in patients with metastatic breast cancer previously treated with conventional anthracyclines: a multicentre phase II trial. *Br J Cancer* 94, 1615-1620.
21. Wu, H. C., Chang, D. K., and Huang, C. T. (2006) Targeted therapy for cancer. *J Cancer Mol* 2, 57-66.
22. Jain, R. K. (1987) Transport of molecules in the tumor interstitium: a review. *Cancer Res* 47, 3039-3051.
23. Willett, C. G., Boucher, Y., di Tomaso, E., Duda, D. G., Munn, L. L., Tong, R. T., Chung, D. C., Sahani, D. V., Kalva, S. P., Kozin, S. V., Mino, M., Cohen, K. S., Scadden, D. T., Hartford, A. C., Fischman, A. J., Clark, J. W., Ryan, D. P., Zhu, A. X., Blaszkowsky, L. S., Chen, H. X., Shellito, P. C., Lauwers, G. Y., and Jain, R. K. (2004) Direct evidence that the VEGF-specific antibody bevacizumab has antivascular effects in human rectal cancer. *Nat Med* 10, 145-147.
24. Mori, T. (2004) Cancer-specific ligands identified from screening of peptide-display libraries. *Curr Pharm Des* 10, 2335-2343.
25. Chen, Y. C., Huang, H. N., Lin, C. T., Chen, Y. F., King, C. C., and Wu, H. C. (2007) Generation and characterization of monoclonal antibodies against dengue virus type 1 for epitope mapping and serological detection by epitope-based peptide antigens. *Clin Vaccine Immunol* 14, 404-411.
26. Liu, I. J., Hsueh, P. R., Lin, C. T., Chiu, C. Y., Kao, C. L., Liao, M. Y., and Wu, H. C. (2004) Disease-specific B Cell epitopes for serum antibodies from patients with severe acute respiratory syndrome (SARS) and serologic detection of SARS antibodies by epitope-based peptide antigens. *The Journal of infectious diseases* 190, 797-809.
27. Wu, H. C., Jung, M. Y., Chiu, C. Y., Chao, T. T., Lai, S. C., Jan, J. T., and Shaio, M. F. (2003) Identification of a dengue virus type 2 (DEN-2) serotype-specific B-cell epitope and detection of DEN-2-immunized animal serum samples using an epitope-based peptide antigen. *The Journal of general virology* 84, 2771-2779.
28. Shadidi, M., and Sioud, M. (2003) Identification of novel carrier peptides for the specific delivery of therapeutics into cancer cells. *Faseb J* 17, 256-258.
29. Zitzmann, S., Mier, W., Schad, A., Kinscherf, R., Askoxylakis, V., Kramer, S., Altmann, A., Eisenhut, M., and Haberkorn, U. (2005) A new prostate carcinoma binding peptide (DUP-1) for tumor imaging and therapy. *Clin Cancer Res* 11, 139-146.
30. Arap, W., Pasqualini, R., and Ruoslahti, E. (1998) Cancer treatment by targeted drug delivery to tumor vasculature in a mouse model. *Science* 279, 377-380.
31. Hoffman, J. A., Giraudo, E., Singh, M., Zhang, L., Inoue, M., Porkka, K., Hanahan, D., and Ruoslahti, E. (2003) Progressive vascular changes in a transgenic mouse model of squamous cell carcinoma. *Cancer Cell* 4, 383-391.
32. Joyce, J. A., Laakkonen, P., Bernasconi, M., Bergers, G., Ruoslahti, E., and Hanahan, D. (2003) Stage-specific vascular markers revealed by phage display in a mouse model of pancreatic islet tumorigenesis. *Cancer Cell* 4, 393-403.
33. Lee, T. Y., Lin, C. T., Kuo, S. Y., K., C. D., and Wu, H. C. (2007) Tumor-homing peptides with targeting to tumor blood vessels of lung cancer for drug delivery. *Cancer Research* 67, 10958-10965.
34. Pastorino, F., Brignole, C., Di Paolo, D., Nico, B., Pezzolo, A., Marimpietri, D., Pagnan, G., Piccardi, F., Cilli, M., Longhi, R., Ribatti, D., Corti, A., Allen, T. M., and Ponzoni, M. (2006) Targeting liposomal chemotherapy via both tumor cell-specific and tumor vasculature-specific ligands potentiates therapeutic efficacy. *Cancer Res* 66, 10073-10082.
35. Giordano, R. J., Cardo-Vila, M., Lahdenranta, J., Pasqualini, R., and Arap, W. (2001) Biopanning and rapid analysis of selective interactive ligands. *Nat Med* 7, 1249-1253.
36. Burroughs, A., Hochhauser, D., and Meyer, T. (2004) Systemic treatment and liver transplantation for hepatocellular carcinoma: two ends of the therapeutic spectrum. *Lancet Oncol* 5, 409-418.
37. Muggia, F. M., Hainsworth, J. D., Jeffers, S., Miller, P., Groshen, S., Tan, M., Roman, L., Uziely, B., Muderspach, L., Garcia, A., Burnett, A., Greco, F. A., Morrow, C. P., Paradiso, L. J., and Liang, L. J. (1997) Phase II study of liposomal doxorubicin in refractory ovarian cancer: antitumor activity and toxicity modification by liposomal encapsulation. *J Clin Oncol* 15, 987-993.
38. Ranson, M. R., Carmichael, J., O'Byrne, K., Stewart, S., Smith, D., and Howell, A. (1997) Treatment of advanced breast cancer with sterically stabilized liposomal doxorubicin: results of a multicenter phase II trial. *J Clin Oncol* 15, 3185-3191.
39. Hong, R. L., Huang, C. J., Tseng, Y. L., Pang, V. F., Chen, S. T., Liu, J. J., and Chang, F. H. (1999) Direct comparison of liposomal doxorubicin with or without polyethylene glycol coating in C-26 tumor-bearing mice: is surface coating with polyethylene glycol beneficial? *Clin Cancer Res* 5, 3645-3652.
40. Hong, R. L., and Tseng, Y. L. (2001) Phase I and pharmacokinetic study of a stable, polyethylene-glycolated liposomal doxorubicin in patients with solid tumors: the relation between pharmacokinetic property and toxicity. *Cancer* 91, 1826-1833.
41. Hong, R. L., and Tseng, Y. L. (2003) A phase II and pharmacokinetic study of pegylated liposomal doxorubicin in patients with advanced hepatocellular carcinoma. *Cancer Chemother Pharmacol* 51, 433-438.
42. Valle, J. W., Dangoor, A., Beech, J., Sherlock, D. J., Lee, S. M., Scarffe, J. H., Swindell, R., and Ranson, M. (2005) Treatment of inoperable hepatocellular carcinoma with pegylated liposomal doxorubicin (PLD): results of a phase II study. *Br J Cancer* 92, 628-630.
43. Schmidinger, M., Wenzel, C., Locker, G. J., Muehlbacher, F., Steininger, R., Gnant, M., Crevenna, R., and Budinsky, A. C. (2001) Pilot study with pegylated liposomal doxorubicin for advanced or unresectable hepatocellular carcinoma. *Br J Cancer* 85, 1850-1852.

TABLE 1

Alignment of phage displayed peptide sequences selected by Mahlavu cells.

| Phage clone | Phage-displayed peptide sequence[a] | SEQ ID NO |
|---|---|---|
| 94 | SFSIIHTPILPL | (SEQ ID NO: 2) |
| 88 | ELMNPLLPFIQP | (SEQ ID NO: 4) |
| 84 | HLPSTGNQYLSL | (SEQ ID NO: 6) |

TABLE 1-continued

Alignment of phage displayed peptide sequences selected by Mahlavu cells.

| Phage clone | Phage-displayed peptide sequence[a] | SEQ ID NO |
|---|---|---|
| 01 | ETNWTHRPPLRV | (SEQ ID NO: 8) |
| 15 | EYRMAHLTPSLL | (SEQ ID NO: 10) |
| 86 | YHLQDSETLSLL | (SEQ ID NO: 12) |
| 42 | SPWYMTPSPNTA | (SEQ ID NO: 14) |
| 72 | SVSVGMKPSPRP | (SEQ ID NO: 16) |
| 47 | DPMTWTPSSVMR | (SEQ ID NO: 18) |
| 26 | TPHRLDWSPHLV | (SEQ ID NO: 20) |
| 02 | GSNPWNTWLTTL | (SEQ ID NO: 22) |
| 62 | NPFNQHLHAQHP | (SEQ ID NO: 24) |
| 09 | SESKDPTLWYPA | (SEQ ID NO: 26) |
| 85 | SFRLATPESSRV | (SEQ ID NO: 28) |
| 12 | SNNEPMLRYTGQ | (SEQ ID NO: 30) |

[a]Phage-displayed consensus amino acid sequences are shown in boldface.

TABLE 2

Phage displayed nucleotide sequences selected by Mahlavu cells.

| Phage clone | Displayed nucleotide sequence | SEQ ID NO: |
|---|---|---|
| 94 | AGTTTTTCGATTATTCATACGCCTATTCTGCCGCTG | (SEQ ID NO: 1) |
| 88 | GAGTTGATGAATCCTCTTTTGCCGTTTATTCAGCCG | (SEQ ID NO: 3) |
| 84 | TCGTTTCGGCTTGCGACTCCTGAGTCTTCGCGTGTT | (SEQ ID NO: 5) |
| 01 | GAGACTAATTGGACTCATAGGCCTCCGCTGCGGGTG | (SEQ ID NO: 7) |
| 15 | GAGTATCGTATGGCGCATCTGACTCCGTCTTTGCTG | (SEQ ID NO: 9) |
| 86 | TATCATCTGCAGGATTCTTAGACTCTGTCTCTGCTT | (SEQ ID NO: 11) |
| 42 | TCTCCTTGGTATATGACTCCTAGTCCTAATACGGCG | (SEQ ID NO: 13) |
| 72 | TCTGTTTCTGTGGGTATGAAGCCGAGTCCTAGGCCT | (SEQ ID NO: 15) |
| 47 | GATCCTATGACTTGGACGCCTAGTAGTGTTATGCGT | (SEQ ID NO: 17) |
| 26 | ACTCCTCATCGTCTGGATTGGTCTCCGCATCTGGTG | (SEQ ID NO: 19) |
| 02 | GGGTCGAATCCTTGGAATACTTGGCTGACTACGCTT | (SEQ ID NO: 21) |
| 62 | AATCCGTTTAATCAGCATCTGCATGCTCAGCATCCT | (SEQ ID NO: 23) |
| 09 | AGTGAGAGTAAGGATCCTACTCTTTGGTATCCTGCG | (SEQ ID NO: 25) |
| 85 | TCGTTTCGGCTTGCGACTCCTGAGTCTTCGCGTGTT | (SEQ ID NO: 27) |
| 12 | CTGCCCAGTATAACGCAGCATCGGCTCATTATTCGA | (SEQ ID NO: 29) |

---

What is claimed is:

1. A purified, synthesized or isolated polypeptide consisting of a polypeptide at least 90% identical to the sequence of SEQ ID NO: 2, wherein the polypeptide comprises SEQ ID NO: 34.

2. The polypeptide of claim 1, wherein the polypeptide is SEQ ID NO: 2.

3. The polypeptide of claim 1, wherein the polypeptide is conjugated to doxorubicin.

4. The polypeptide of claim 2, wherein the polypeptide is conjugated to doxorubicin.

5. A fusion protein comprising a first polypeptide fused to a second polypeptide, wherein the first polypeptide is the polypeptide of claim 1.

6. A fusion protein comprising a first polypeptide fused to a second polypeptide, wherein the first polypeptide is the polypeptide of claim 2.

7. A liposome comprising at least one polypeptide of claim 1.

8. The liposome of claim 7, wherein the polypeptide is SEQ ID NO: 2.

9. The liposome of claim 7, wherein the liposome further comprises doxorubicin.

\* \* \* \* \*